United States Patent
Ghosh et al.

(10) Patent No.: US 10,773,085 B2
(45) Date of Patent: Sep. 15, 2020

(54) QRS OFFSET AND ONSET DETERMINATION

(71) Applicant: Medtronic, Inc., Minneapolis, MN (US)

(72) Inventors: Subham Ghosh, Blaine, MN (US); D'Anne Kudlik, Lino Lakes, MN (US); Ya-Jian Cheng, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 139 days.

(21) Appl. No.: 15/915,995

(22) Filed: Mar. 8, 2018

(65) Prior Publication Data

US 2018/0263522 A1    Sep. 20, 2018

Related U.S. Application Data

(60) Provisional application No. 62/471,938, filed on Mar. 15, 2017.

(51) Int. Cl.
*A61B 5/04* (2006.01)
*A61N 1/365* (2006.01)
(Continued)

(52) U.S. Cl.
CPC ............ *A61N 1/365* (2013.01); *A61B 5/0408* (2013.01); *A61B 5/0422* (2013.01); *A61B 5/0452* (2013.01); *A61B 5/0456* (2013.01); *A61B 5/04085* (2013.01); *A61B 5/04525* (2013.01); *A61B 5/686* (2013.01); *A61B 5/6823* (2013.01); *A61B 5/7203* (2013.01); *A61B 5/7264* (2013.01); *A61N 1/3622* (2013.01); *A61N 1/371* (2013.01); *A61N 1/3704* (2013.01); *A61B 5/0428* (2013.01); *A61B 5/0472* (2013.01);
(Continued)

(58) Field of Classification Search
CPC ... A61B 5/0428; A61B 5/7203; A61B 5/7278; A61B 5/686; A61B 5/7264; A61B 5/04085; A61B 5/0422; A61B 5/0452; A61B 5/6823; A61B 5/6852
See application file for complete search history.

(56) References Cited

U.S. PATENT DOCUMENTS 4,233,987 A    11/1980    Feingold
4,402,323 A    9/1983    White
(Continued)

FOREIGN PATENT DOCUMENTS

CN    1043621 A    7/1990
CN    1253761 A    5/2000
(Continued)

OTHER PUBLICATIONS

International Patent Application No. PCT/US2018/022133, filed Mar. 13, 2018; International Search Report and Written Opinion, dated May 29, 2018; 16 pages.
(Continued)

*Primary Examiner* — Mallika D Fairchild

(57) ABSTRACT

The exemplary systems and methods may be configured to generate a dispersion signal from a plurality of cardiac signals and determine a QRS onset time value and a QRS offset time value from the plurality of cardiac signals. The QRS onset and offset time values may be used to measure, or capture, activation times.

26 Claims, 23 Drawing Sheets

(51) Int. Cl.
*A61N 1/37* (2006.01)
*A61B 5/0452* (2006.01)
*A61N 1/362* (2006.01)
*A61B 5/00* (2006.01)
*A61B 5/042* (2006.01)
*A61B 5/0408* (2006.01)
*A61B 5/0456* (2006.01)
*A61B 5/0472* (2006.01)
*A61B 5/0428* (2006.01)

(52) U.S. Cl.
CPC .......... *A61B 5/6801* (2013.01); *A61B 5/6852* (2013.01); *A61B 5/7217* (2013.01); *A61B 5/7278* (2013.01)

(56) References Cited

U.S. PATENT DOCUMENTS

| | | | |
|---|---|---|---|
| 4,428,378 A | 1/1984 | Anderson et al. | |
| 4,497,326 A | 2/1985 | Curry | |
| 4,566,456 A | 1/1986 | Koning et al. | |
| 4,593,702 A | 6/1986 | Kepski | |
| 4,674,511 A | 6/1987 | Cartmell | |
| 4,763,660 A | 8/1988 | Kroll et al. | |
| 4,777,955 A | 10/1988 | Brayten et al. | |
| 4,787,389 A | 11/1988 | Tarjan | |
| 4,974,598 A * | 12/1990 | John | A61B 5/04085 600/509 |
| 4,979,507 A | 12/1990 | Heinz et al. | |
| 5,052,388 A | 10/1991 | Sivula et al. | |
| 5,054,496 A | 10/1991 | Wen et al. | |
| 5,311,873 A | 5/1994 | Savard et al. | |
| 5,331,960 A | 7/1994 | Lavine | |
| 5,334,220 A | 8/1994 | Sholder | |
| 5,443,492 A | 8/1995 | Stokes et al. | |
| 5,485,849 A | 1/1996 | Panescu et al. | |
| 5,514,163 A | 5/1996 | Markowitz et al. | |
| 5,552,645 A | 9/1996 | Weng | |
| 5,628,778 A | 5/1997 | Kruse et al. | |
| 5,671,752 A | 9/1997 | Sinderby et al. | |
| 5,683,429 A | 11/1997 | Mehra | |
| 5,683,432 A | 11/1997 | Goedeke et al. | |
| 5,687,737 A | 11/1997 | Branham et al. | |
| 5,810,740 A | 9/1998 | Paisner | |
| 5,876,336 A | 3/1999 | Swanson et al. | |
| 5,891,045 A | 4/1999 | Albrecht et al. | |
| 5,922,014 A | 7/1999 | Warman et al. | |
| 6,055,448 A | 4/2000 | Anderson et al. | |
| 6,128,535 A | 10/2000 | Maarse et al. | |
| 6,141,588 A | 10/2000 | Cox et al. | |
| 6,187,032 B1 | 2/2001 | Ohyu et al. | |
| 6,205,357 B1 | 3/2001 | Ideker et al. | |
| 6,226,542 B1 | 5/2001 | Reisfeld | |
| 6,236,883 B1 | 5/2001 | Ciaccio et al. | |
| 6,243,603 B1 | 6/2001 | Ideker et al. | |
| 6,246,898 B1 | 6/2001 | Vesely et al. | |
| 6,301,496 B1 | 10/2001 | Reisfeld | |
| 6,311,089 B1 | 10/2001 | Mann et al. | |
| 6,330,476 B1 | 12/2001 | Ben-Haim et al. | |
| 6,358,214 B1 | 3/2002 | Tereschouk | |
| 6,377,856 B1 | 4/2002 | Carson | |
| 6,381,493 B1 | 4/2002 | Stadler et al. | |
| 6,393,316 B1 | 5/2002 | Gillberg et al. | |
| 6,418,346 B1 | 7/2002 | Nelson et al. | |
| 6,442,433 B1 | 8/2002 | Linberg | |
| 6,456,867 B2 | 9/2002 | Reisfeld | |
| 6,473,638 B2 | 10/2002 | Ferek-Petric | |
| 6,480,745 B2 | 11/2002 | Nelson et al. | |
| 6,484,118 B1 | 11/2002 | Govari | |
| 6,507,756 B1 | 1/2003 | Heynen et al. | |
| 6,532,379 B2 | 3/2003 | Stratbucker | |
| 6,584,343 B1 | 6/2003 | Ransbury et al. | |
| 6,599,250 B2 | 7/2003 | Webb et al. | |
| 6,625,482 B1 | 9/2003 | Panescu et al. | |
| 6,640,136 B1 | 10/2003 | Helland et al. | |
| 6,650,927 B1 | 11/2003 | Keidar | |
| 6,766,189 B2 | 7/2004 | Yu et al. | |
| 6,772,004 B2 | 8/2004 | Rudy | |
| 6,804,555 B2 | 10/2004 | Warkentin | |
| 6,847,836 B1 | 1/2005 | Sujdak | |
| 6,856,830 B2 | 2/2005 | He | |
| 6,882,882 B2 | 4/2005 | Struble et al. | |
| 6,885,889 B2 | 4/2005 | Chinchoy | |
| 6,915,149 B2 | 7/2005 | Ben-Haim | |
| 6,968,237 B2 | 11/2005 | Doan et al. | |
| 6,975,900 B2 | 12/2005 | Rudy et al. | |
| 6,978,184 B1 | 12/2005 | Marcus et al. | |
| 6,980,675 B2 | 12/2005 | Evron et al. | |
| 7,016,719 B2 | 3/2006 | Rudy et al. | |
| 7,031,777 B2 | 4/2006 | Hine et al. | |
| 7,058,443 B2 | 6/2006 | Struble | |
| 7,062,315 B2 | 6/2006 | Koyrakh et al. | |
| 7,092,759 B2 | 8/2006 | Nehls et al. | |
| 7,142,922 B2 | 11/2006 | Spinelli et al. | |
| 7,184,835 B2 | 2/2007 | Kramer et al. | |
| 7,215,998 B2 | 5/2007 | Wesselink et al. | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,313,444 B2 | 12/2007 | Pianca et al. | |
| 7,321,677 B2 | 1/2008 | Evron et al. | |
| 7,346,381 B2 | 3/2008 | Okerlund et al. | |
| 7,398,116 B2 | 7/2008 | Edwards | |
| 7,426,412 B1 | 9/2008 | Schecter | |
| 7,454,248 B2 | 11/2008 | Burrell et al. | |
| 7,499,743 B2 | 3/2009 | Vass et al. | |
| 7,509,170 B2 | 3/2009 | Zhang et al. | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,610,088 B2 | 10/2009 | Chinchoy | |
| 7,613,500 B2 | 11/2009 | Vass et al. | |
| 7,616,993 B2 | 11/2009 | Milssig et al. | |
| 7,664,550 B2 | 2/2010 | Eick et al. | |
| 7,684,863 B2 | 3/2010 | Parikh et al. | |
| 7,742,629 B2 | 6/2010 | Zarkh et al. | |
| 7,747,047 B2 | 6/2010 | Okerlund et al. | |
| 7,751,882 B1 | 7/2010 | Helland et al. | |
| 7,769,451 B2 | 8/2010 | Yang et al. | |
| 7,778,685 B2 | 8/2010 | Evron et al. | |
| 7,778,686 B2 | 8/2010 | Vass et al. | |
| 7,787,951 B1 | 8/2010 | Min | |
| 7,813,785 B2 | 10/2010 | Okerlund et al. | |
| 7,818,040 B2 | 10/2010 | Spear et al. | |
| 7,848,807 B2 | 12/2010 | Wang | |
| 7,860,580 B2 | 12/2010 | Falk et al. | |
| 7,894,889 B2 | 2/2011 | Zhang | |
| 7,912,544 B1 | 3/2011 | Min et al. | |
| 7,917,214 B1 | 3/2011 | Gill et al. | |
| 7,941,213 B2 | 5/2011 | Markowitz et al. | |
| 7,953,475 B2 | 5/2011 | Harley et al. | |
| 7,953,482 B2 | 5/2011 | Hess | |
| 7,983,743 B2 | 7/2011 | Rudy et al. | |
| 7,996,063 B2 | 8/2011 | Vass et al. | |
| 7,996,070 B2 | 8/2011 | van Dam et al. | |
| 8,010,194 B2 | 8/2011 | Muller | |
| 8,019,402 B1 | 9/2011 | Kryzpow et al. | |
| 8,019,409 B2 | 9/2011 | Rosenberg et al. | |
| 8,032,229 B2 | 10/2011 | Gerber et al. | |
| 8,036,743 B2 | 10/2011 | Savage et al. | |
| 8,060,185 B2 | 11/2011 | Hunter et al. | |
| 8,150,513 B2 | 4/2012 | Chinchoy | |
| 8,160,700 B1 | 4/2012 | Ryu et al. | |
| 8,175,703 B2 | 5/2012 | Dong et al. | |
| 8,180,428 B2 | 5/2012 | Kaiser et al. | |
| 8,195,292 B2 | 6/2012 | Rosenberg et al. | |
| 8,213,693 B1 | 7/2012 | Li | |
| 8,214,041 B2 | 7/2012 | Van Gelder et al. | |
| 8,265,738 B1 | 9/2012 | Min et al. | |
| 8,285,377 B2 | 10/2012 | Rosenberg et al. | |
| 8,295,943 B2 | 10/2012 | Eggen et al. | |
| 8,326,419 B2 | 12/2012 | Rosenberg et al. | |
| 8,332,030 B2 | 12/2012 | Hess et al. | |
| 8,380,308 B2 | 2/2013 | Rosenberg et al. | |

(56) References Cited

U.S. PATENT DOCUMENTS

| | | |
|---|---|---|
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et el. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2005/0197674 A1* | 9/2005 | McCabe .............. A61B 5/0402 607/9 |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0184297 A1 | 7/2011 | Vitali et al. |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |

(56) References Cited

U.S. PATENT DOCUMENTS

| | | |
|---|---|---|
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0107507 A1 | 4/2014 | Ghosh et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0022164 A1 | 1/2016 | Brockway et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/005900 A1 | 1/2003 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

Kemmelings et al., "Automatic QRS detection during body surface mapping of ventricular tachycardia," *Proceedings of the Annual International Conference of the IEEE Engineering in Medicine and Biology Society*, Oct. 29-Nov. 1, 1992, IEEE, New York, NY, US, 561-562.

International Search Report and Written Opinion dated May 3, 2012 for International Application No. PCT/US2012/036262; 9 pages.

International Search Report and Written Opinion dated May 3, 2012 for International Application No. PCT/US2012/036302; 9 pages.

International Search Report and Written Opinion dated Aug. 6, 2014 for International Application No. PCT/US2014/036153; 14 pages.

International Search Report and Written Opinion dated Nov. 7, 2014 for International Application No. PCT/US2014/036163; 12 pages.

International Search Report and Written Opinion dated Oct. 28, 2014 for International Application No. PCT/US2014/041928; 15 pages.

International Search Report and Written Opinion dated Oct. 24, 2014 for International Application No. PCT/US2014/041929; 14 pages.

International Search Report and Written Opinion dated Nov. 4, 2014 for International Application No. PCT/US2014/0247583; 7 pages.

International Search Report and Written Opinion dated Nov. 12, 2014 for International Application No. PCT/US2014/047971; 7 pages.

International Search Report and Written Opinion dated Nov. 12, 2014 for International Application No. PCT/US2014/048120; 7 pages.

International Search Report and Written Opinion dated Mar. 9, 2015 for International Application No. PCT/US2014/069214; 11 pages.

(56) References Cited

OTHER PUBLICATIONS

International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," *Circulation*, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" *J. Am. Coll. Cardiol.* 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—a Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric

(56) References Cited

OTHER PUBLICATIONS

Remodeling During Cardiac Resynchronization Therapy," *Circulation*, Feb. 9, 2010; 121(5):626-34. Available online Jan. 25, 2010.

Sweeney et al., QRS Fusion Complex Analysis Using Wave Interference to Predict Reverse Remodeling During Cardiac Resynchronization Therapy, heart Rhythm, 2014, 11:806-813.

Turner et al, "Electrical and Mechanical Components of Dyssynchrony in Heart Failure Patients with Normal QRS Duration and Left Bundle-Branch Block," *Circulation* 2004; 109:2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

\* cited by examiner

FIG. 9
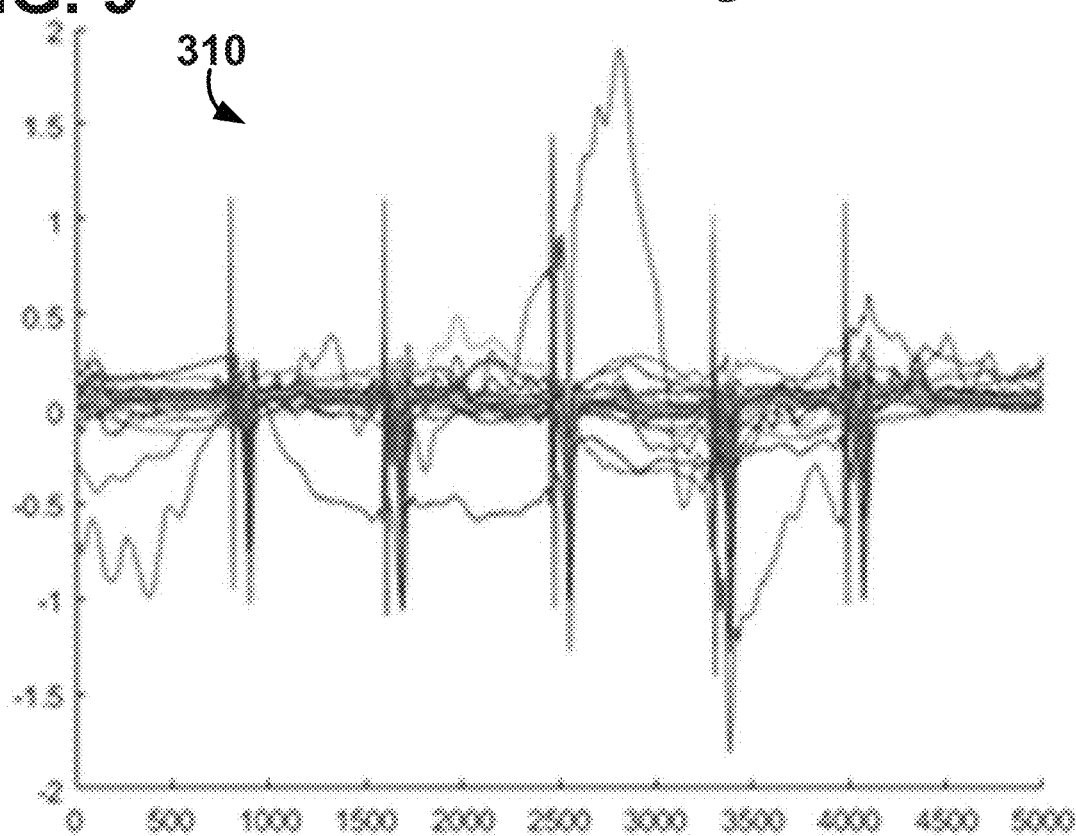
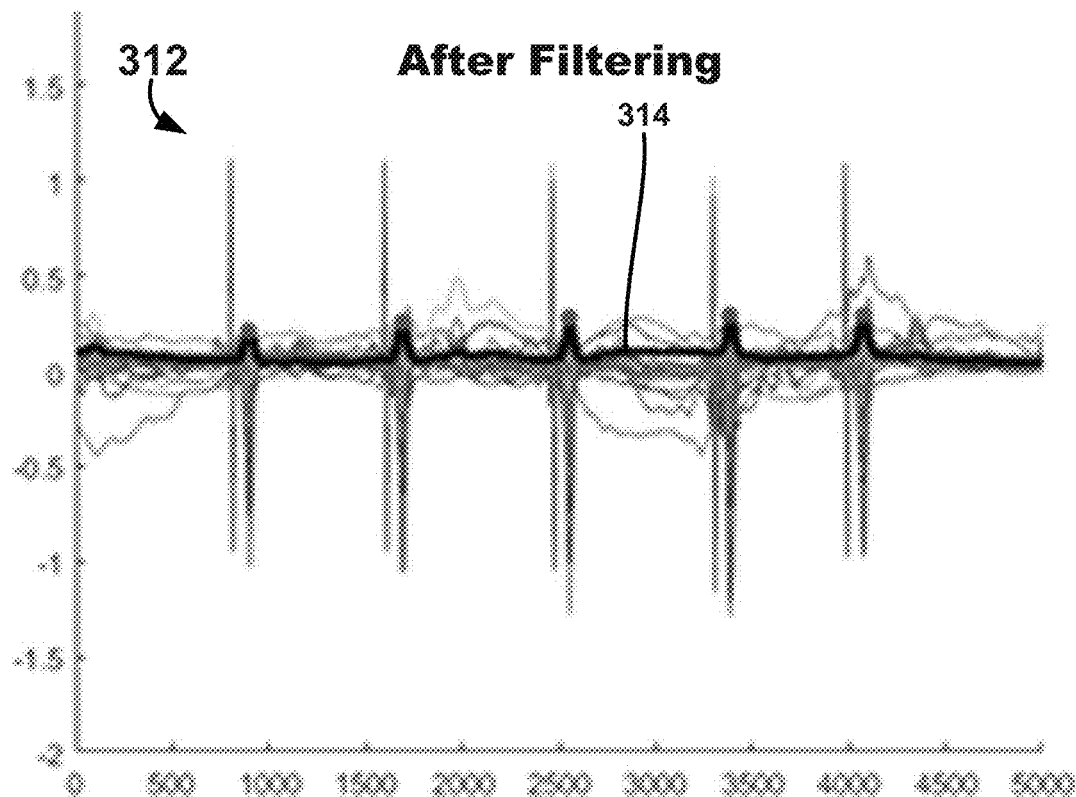

QRS OFFSET AND ONSET DETERMINATION

This application claims the benefit of U.S. Provisional Application Ser. No. 62/471,938, filed Mar. 15, 2017, the entire contents of which are incorporated by reference herein in their entirety.

The disclosure herein relates to systems and methods for use in the determination of QRS onset and offset time values from a plurality of cardiac signals.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy. Instead, the systems, methods, and interfaces may use electrical measurements taken noninvasively using, e.g., a plurality of external electrodes attached to the skin of a patient about the patient's torso.

In one or more embodiments, the systems, methods, and interfaces may use, or include, implantable devices such as leads, probes, implantable electrodes, etc. to monitor, or acquire, a plurality of cardiac signals from tissue of the patient for use in evaluating the patient and/or cardiac therapy. For example, the systems, methods, and interfaces may use electrical measurements taken using, e.g., a plurality of implantable electrodes either implanted long term or temporarily within a patient.

One exemplary system may include electrode apparatus and computing apparatus comprising one or more processors and coupled to the electrode apparatus. The electrode apparatus may include a plurality of electrodes to monitor electrical activity from tissue of a patient. The computing apparatus may be configured to monitor electrical activity using the plurality of electrodes to generate a plurality of cardiac signals over time and generate a dispersion signal from the plurality of cardiac signals. The dispersion signal may be representative of the dispersion of the plurality of cardiac signals over time. The computing apparatus may be further configured to determine a QRS onset time value and a QRS offset time value for each of at least one QRS complex within the monitored electrical activity based on the dispersion signal.

One exemplary method may include monitoring electrical activity from tissue of a patient using a plurality of electrodes to generate a plurality of cardiac signals over time and generating a dispersion signal from the plurality of cardiac signals. The dispersion signal may be representative of the dispersion of the plurality of cardiac signals over time. The exemplary method may further include determining a QRS onset time value and a QRS offset time value for each of at least one QRS complex within the monitored electrical activity based on the dispersion signal.

In one or more embodiments, the computing apparatus may be further configured to execute or the method may further include determining an activation time for each of the at least one QRS complex within each of the plurality of cardiac signals within the QRS duration between the QRS onset and offset time values corresponding to the at least one QRS complex. Further, the computing apparatus may be further configured to execute or the method may further include determining at least one metric of electrical heterogeneity based on the activation time for each of the at least one QRS complex within each of the plurality of cardiac signals.

In one or more embodiments, the plurality of electrodes may include a plurality of external electrodes to be located proximate the patient's skin and/or a plurality of internal electrodes to be located within the patient. In one or more embodiments, generating a dispersion signal from the plurality of cardiac signals may include determining a standard deviation of the plurality of cardiac signals over time.

In one or more embodiments, the computing apparatus may be further configured to execute or the method may further include selecting a portion of the dispersion signal over a selected time period. Determining a QRS onset time value and a QRS offset time value for each of at least one QRS complex within the monitored electrical activity based on the dispersion signal may include comprise determining the QRS onset time value and the QRS offset time value for each of the at least one QRS complex within the monitored electrical activity of the selected time period based on the selected portion of the dispersion signal. In one or more embodiments, the selected time period may be less than or equal to 5 seconds.

In one or more embodiments, determining a QRS onset time value and a QRS offset time value for each of at least one QRS complex within the monitored electrical activity based on the dispersion signal may further include determining a maximum dispersion value of the dispersion signal and determining the QRS onset time value and the QRS offset time value using the maximum dispersion value. In one or more embodiments, determining a QRS onset time value and a QRS offset time value for each of at least one QRS complex within the monitored electrical activity based on the dispersion signal may further include filtering the dispersion signal to remove one or more values of the dispersion signal that are less than or equal to a selected percentage of the maximum dispersion value of the dispersion signal. In one or more embodiments, determining a QRS onset time value and a QRS offset time value for each of at least one QRS complex within the monitored electrical activity based on the dispersion signal may further include filtering the dispersion signal to remove one or more dispersion values of the dispersion signal corresponding to at least one of a T-wave and a P-wave in the plurality of cardiac signals.

In one or more embodiments, determining a QRS onset time value and a QRS offset time value for each of at least one QRS complex within the monitored electrical activity based on the dispersion signal may further include determining a minimum dispersion value of the dispersion signal within a first time period before a maximum dispersion value of the dispersion signal to determine the QRS onset time value and determining a minimum dispersion value of the dispersion signal within a second time period after the maximum dispersion value of the dispersion signal to determine the QRS offset time value. In one or more embodiments, each of the first and second time periods may be less than or equal to 120 milliseconds. In one or more embodiments, each of the first and second time periods may be less than or equal to 200 milliseconds.

In one or more embodiments, determining a QRS onset time value and a QRS offset time value for each of at least one QRS complex within the monitored electrical activity based on the dispersion signal may further include determining a latest dispersion value of the dispersion signal within a first time period before a maximum dispersion value of the dispersion signal that is less than or equal to a selected percentage of a minimum dispersion value of the dispersion signal within the first time period to determine the QRS onset time value and determining an earliest dispersion value of the dispersion signal within a second time period after the maximum dispersion value of the dispersion signal that is less than or equal to a selected percentage of a minimum dispersion value of the dispersion signal within the second time period to determine the QRS onset time value In one or more embodiments, the computing apparatus may be further configured to execute or the method may further include determining an absolute amplitude between the QRS onset time value and the QRS offset time value for each of the at least QRS complex for each of the plurality of cardiac signals, selecting one or more cardiac signals of the plurality of cardiac signals based on the absolute amplitude, and determining an activation time for each of the at least one QRS complex within each of the selected one or more cardiac signals within the QRS duration between the QRS onset and offset time values corresponding to the at least one QRS complex. In one or more embodiments, selecting one or more cardiac signals of the plurality of cardiac signals based on the absolute amplitude may include selecting one or more cardiac signals of the plurality of cardiac signals defining an absolute amplitude greater than or equal to a threshold value, and the threshold value may be less than the median absolute amplitude of the plurality of cardiac signals.

In one or more embodiments, the computing apparatus may be further configured to execute or the method may further include removing one or more noisy cardiac signals from the plurality of cardiac signals prior to determining the dispersion signal. Further, in one or more embodiments, the one or more noisy cardiac signals may be identified by identifying cardiac signals comprising absolute areas-under-the-curve greater than or equal to a threshold value. In one or more embodiments, the at least one QRS complex may include a plurality of QRS complexes In one or more embodiments, the computing apparatus may be further configured to execute or the method may further include adjusting cardiac therapy in response to one or more metrics derived using the determined QRS onset and offset time values and/or displaying on a graphical user interface one or more metrics derived using the determined QRS onset and offset time values. Further, the one or more metrics may include activation time of each of the plurality of cardiac signals.

Electrode apparatus (e.g., an "ECG belt") may be used for various cardiac resynchronization therapy (CRT) applications including optimizing lead location/pacing pacing parameters, etc. based on one or more metrics of electrical heterogeneity derived from activation times computed from the multiple electrodes on the body-surface. Determination of activation times may include determination of the earliest onset and the latest offset of QRS complex (depolarization activity) based on cardiac signals, or electrocardiogram (ECG) signals, from all the electrodes on the body-surface.

Various systems and methods may identify a QRS onset/offset from a single cardiac signal or channel of an ECG. To repeat the single-channel QRS onset/offset identification, or determination, for a multitude of channels may involve considerable computational expense. The exemplary systems and methods disclosed herein may be described as enabling automatic determination of QRS onset and offset time values based on a single, composite time-varying signal which at any time-instant represents the dispersion (e.g., standard deviation) of amplitudes across all, or at least more than one, cardiac signals/ECG channels on the body-surface of the patient.

Further, the exemplary systems and methods may isolate the QRS complex using a dispersion measurement across all, or more than one, electrodes determined to be in, or make, contact with the body-surface (e.g., based on impedance) at each sampled time point. The dispersion measurement may refer to any measurement that takes advantage of the differences in signal magnitude and polarity across multiple channels collected during body surface mapping—including but not limited to—standard deviation, coefficient of variance, range, and absolute deviations, often taken about a measure of central tendency like mean, mode or median. Still further, the exemplary systems and methods may establish a threshold criterion to eliminate noisy channels from electrocardiographic measurements from the body surface mapping to, e.g., bolster the accuracy and confidence of the determinations.

The exemplary systems and methods may be used for applications where cardiac depolarization onset and offset time values are identified from data involving a multitude of ECG/far-field EGMs for determination of activation times (e.g., body-surface mapping) and mapping from a constellation catheter-basket or a balloon with multiple unipolar electrodes inside a heart cavity (e.g. RV or LV) for beat-by-beat, simultaneous mapping of electrical activity.

In one or more embodiments, the exemplary systems and methods may be described as using QRS peak detection using a dispersion measurement. At each time point, the dispersion measurement may be calculated across all cardiac signals, or ECG channels. The maximum dispersion in a local window of time may be calculated, and a threshold dependent on the maximum dispersion value (e.g., a local maximum dispersion value within a time window) may be calculated. The first point in the window where the signal reaches the locally-determined dispersion threshold may be used to determine the peak, or maximum value, of the QRS complex. It may be described that the exemplary systems and methods may obtain, or get, a window, or local area of time, find a maximum dispersion within the window, and set a threshold based on the maximum (e.g., 75% of max). At the first point where this threshold is reached in the window, the next local maximum may be determined, which will be identified as the QRS peak or maximum dispersion value for the window.

In another embodiment, which does not use a threshold, the signals from the electrodes are high-pass filtered to reduce T-wave and P-wave activity, the single dispersion signal may be generated from the filtered signals, and the signal acquisition may be performed in short time periods (e.g., 1000 milliseconds) to include only one or two cardiac cycles whose peak QRS can be identified by finding the maximum amplitude of the dispersion signal.

In one or more embodiments, the exemplary systems and methods may be described as detecting QRS complex onset and offset using a dispersion measurement. Using the previously-determined QRS peaks, each QRS complex onset may be determined by identifying the time of minimum dispersion or of a selected percentage of the minimum dispersion (e.g., with 10% of the minimum dispersion) in a local time frame (e.g., window of time, selected time period, etc.) prior to each QRS peak. Similarly, each QRS offset may be determined by identifying the time of minimum dispersion or of a selected percentage of the minimum dispersion (e.g., with 10% of the minimum dispersion) in a local time frame (e.g., window of time, selected time period, etc.) after each QRS peak.

In one or more embodiments, the exemplary systems and methods may be described as being configured to eliminate noisy channels. To reduce the number of noisy channels, a software-level threshold of QRS complex amplitude maybe established. After the QRS onset and offset are determined, the absolute (e.g., peak-to-peak) amplitude between the onset and offset values may be calculated for each cardiac signal or ECG channel. A threshold may then be established at some fraction of the median absolute amplitude value. Any cardiac signal or ECG channel with an amplitude less than the determined, or calculated, threshold may not be used for computation of activation times.

Automatic signal feature isolation and noise reduction for body surface mapping calculations may be described as streamlining calculations for various cardiac patient evaluation and/or therapy evaluation tools. As a result, patient-level data analysis may be more accurate and consistent and may further simplify the role of the physician, which may increase the efficiency of patient assessment. Further, the exemplary systems and methods may be described as being useful for automated processing of electrical activation maps that can be integrated with other automated routines in other devices.

In one or more embodiments, the exemplary systems and methods may be used to adjust cardiac therapy configurations and determine onset, offset and duration of QRS complexes and the resulting heterogeneity of activation resulting from the new cardiac device configuration. Further, any changes to the electrical heterogeneity from a baseline condition may be displayed on a graphical user interface. Further, users may select one or more cardiac therapy configurations based on changes in heterogeneity, and the exemplary systems and methods may assist the users in doing so.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 9 is an exemplary graph of a dispersion signal overlaid over a plurality of cardiac signals that were unfiltered and an exemplary graph of a dispersion signal overlaid over the plurality of cardiac signals after filtering.

DETAILED DESCRIPTION OF EXEMPLARY EMBODIMENTS

Figure 1:
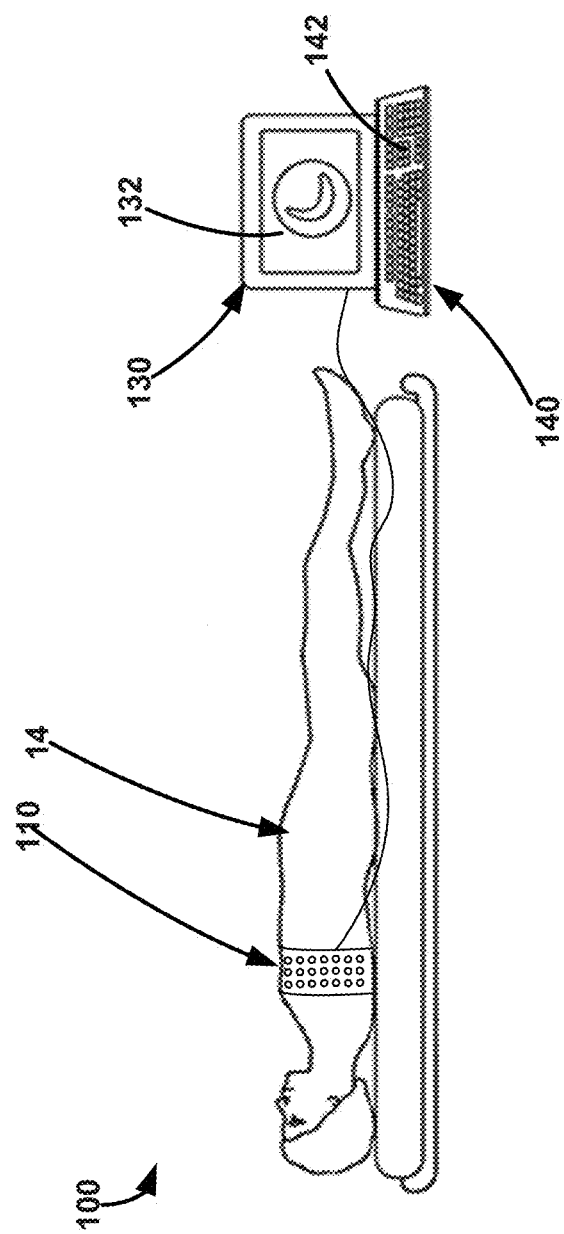
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-21. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical activation times can be detected or estimated in proximity of a reference location (e.g., which can be a chosen location for the left ventricle lead during implant) using unipolar electrocardiogram (ECG) recordings. Such electrical activation times may be measured and displayed, or conveyed, to an implanter by a system which acquires the ECG signals and generates the metric of electrical activation times (e.g., depolarization) measured from various ECG locations.

Various exemplary systems, methods, and interfaces may be configured to use electrode apparatus including external electrodes, display apparatus, and computing apparatus to noninvasively assist a user (e.g., a physician) in the evaluation of a patient's condition and/or cardiac therapy being performed on a patient. An exemplary system 100 including electrode apparatus 110, display apparatus 130, and computing apparatus 140 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate or select a pacing electrode or pacing vector proximate the patient's heart in conjunction with the evaluation of cardiac therapy.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy evaluation including determining location information (e.g., location information for the electrodes). Exemplary systems and methods that use imaging apparatus and/or electrode apparatus may be described in U.S. patent application Ser. No. 13/916,353 filed on Jun. 12, 2013 and entitled "Implantable Electrode Location Selection," U.S. patent application Ser. No. 13/916,377 filed on Jun. 12, 2013 and entitled "Implantable Electrode Location Selection," U.S. patent application Ser. No. 14/227,955 filed on Mar. 27, 2014 and entitled "Systems, Methods, and Interfaces for Identifying Effective Electrodes," U.S. patent application Ser. No. 14/227,919 filed on Mar. 27, 2014 and entitled "Systems, Methods, and Interfaces for Identifying Optical Electrical Vectors," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al.

issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating a pacing location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.)

containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user. Further, the computing apparatus 140 may be described as including one or more processors or processing circuitry configured to execute the illustrative processes, methods, and algorithms described herein.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
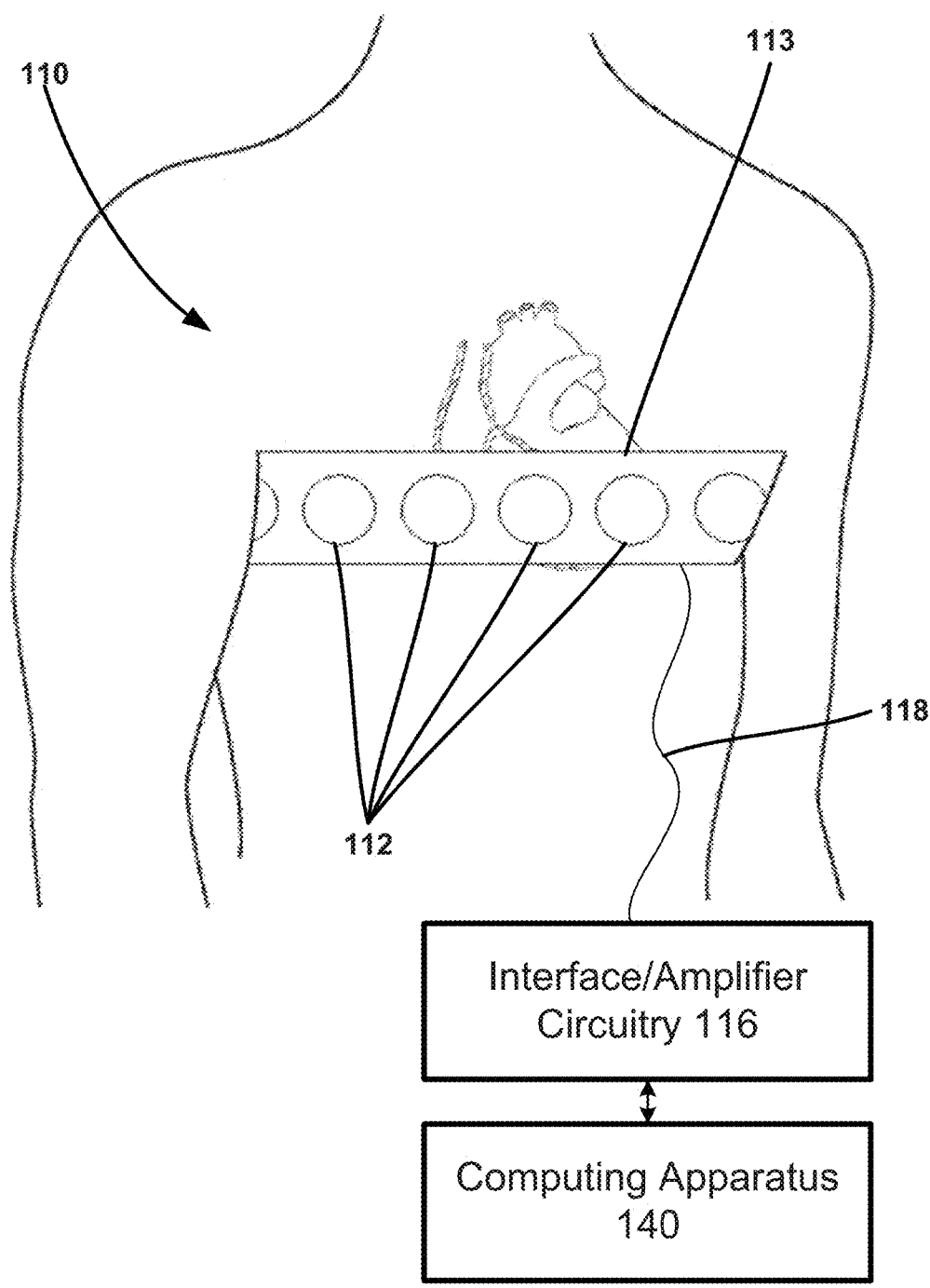
FIGS. 2-3 are diagrams of exemplary external electrode apparatus for measuring torso-surface potentials.

Electrical activation times of the patient's heart may be useful to evaluate a patient's cardiac condition and/or cardiac therapy being delivered to a patient. Surrogate electrical activation information or data of one or more regions of a patient's heart may be monitored, or determined, using electrode apparatus 110 as shown in FIG. 1 and in FIG. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation information or data such as surrogate cardiac electrical activation times, e.g., representative of actual, or local, electrical activation times of one or more regions of the patient's heart as will be further described herein. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and the next onset of cardiac depolarization. In one or more embodiments, measurement of activation times can be performed by measuring the period of time between an onset of cardiac depolarization (e.g., onset of QRS complex) and conclusion of cardiac repolarization (e.g., offset of QRS complex). In one or more embodiments, measurement of activation times can be performed by picking an appropriate fiducial point (e.g., peak values, minimum values, minimum slopes, maximum slopes, zero crossings, threshold crossings, etc. of a near or far-field EGM) and measuring time between fiducial points (e.g., within the electrical activity).

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient's cardiac condition and/or cardiac therapy being delivered to the patient.

Figure 3:
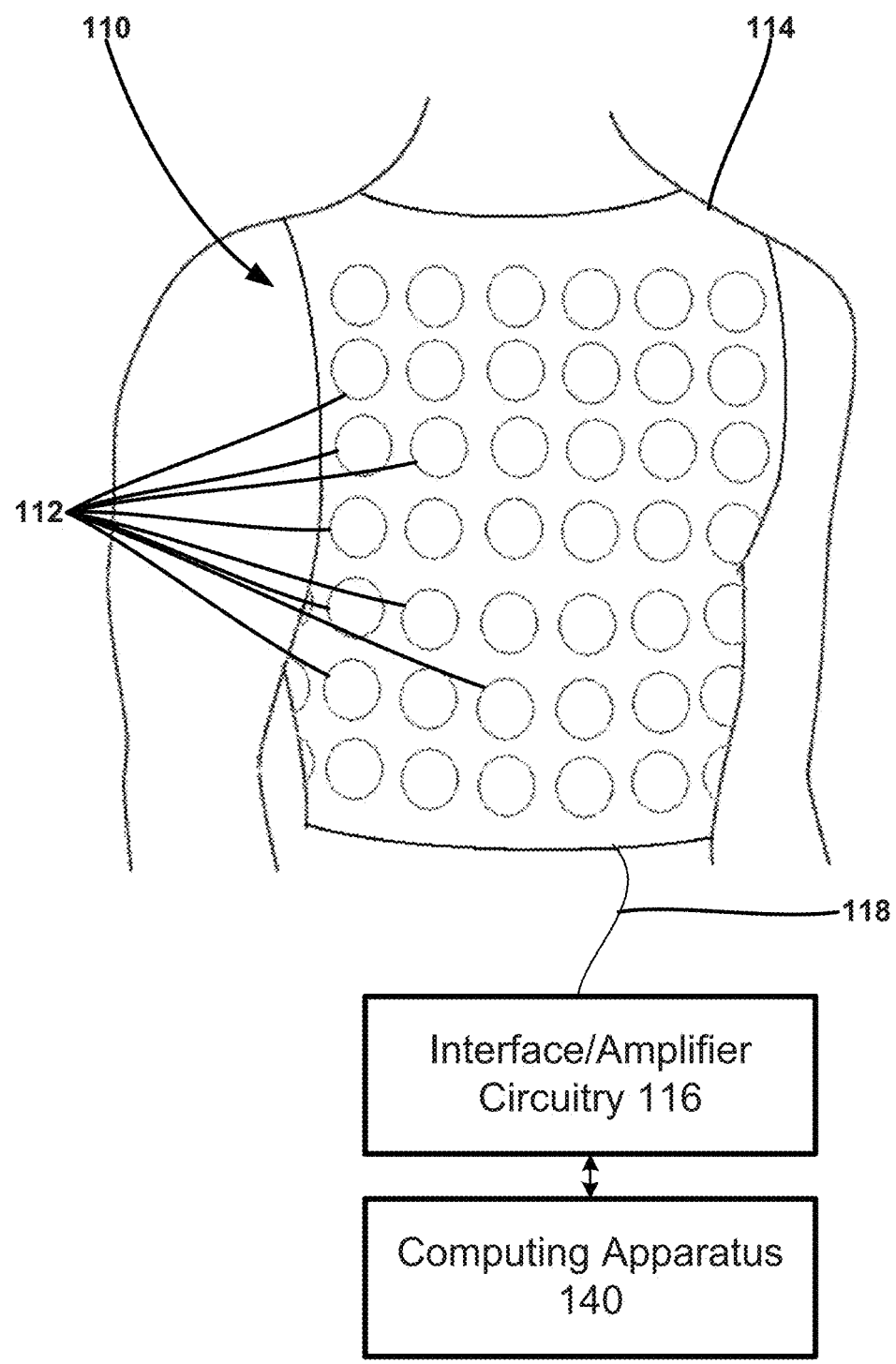

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used to provide noninvasive assistance to a user in the evaluation of a patient's cardiac health or status, and/or the valuation of cardiac therapy (e.g., cardiac therapy being presently-delivered to a patient during implantation or after implantation). Further, the exemplary systems, methods, and interfaces may be used to assist a user in the configuration of the cardiac therapy being delivered to a patient.

Figure 4:
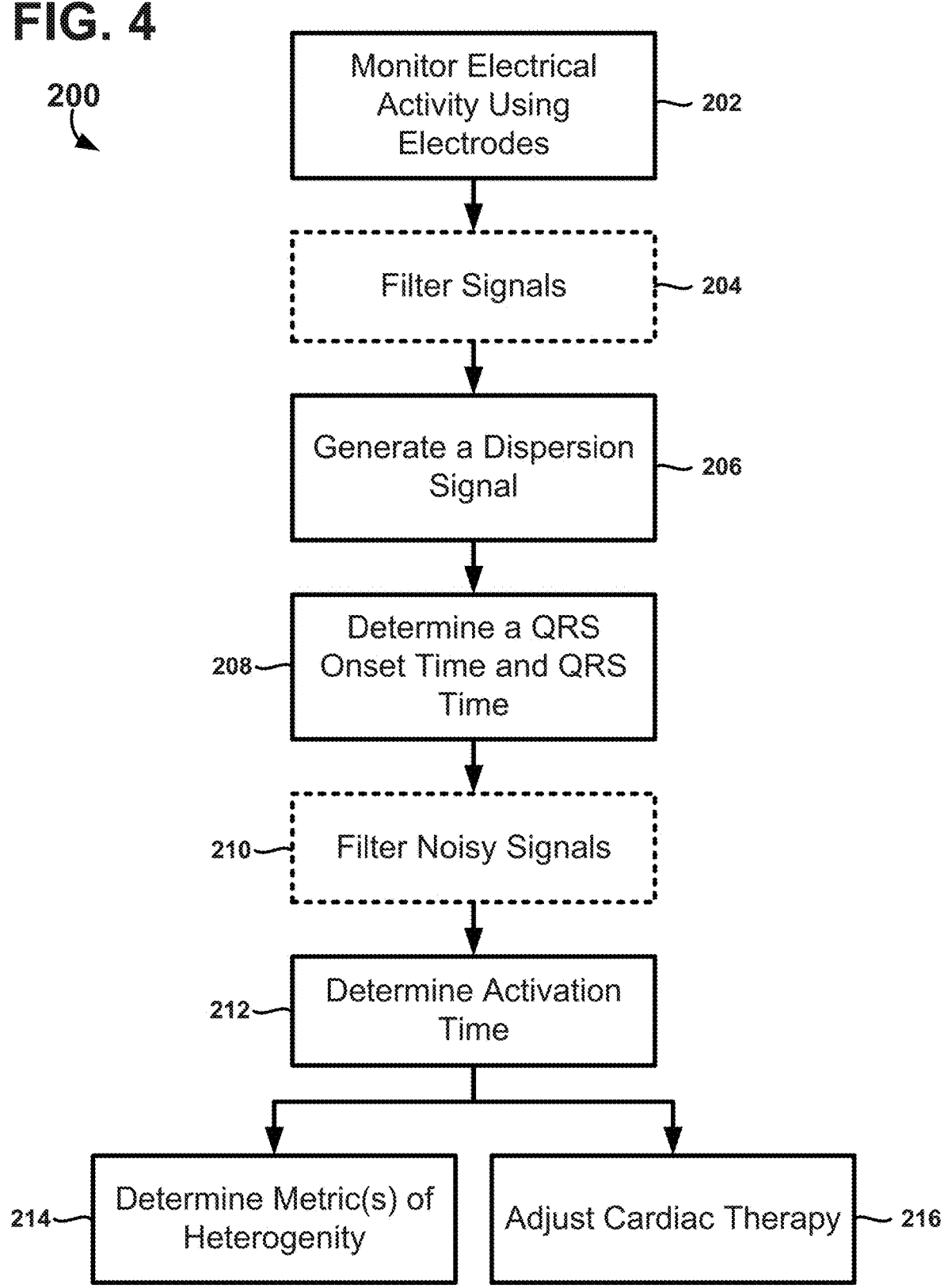
FIG. 4 is a block diagram of an exemplary method for determining QRS duration from a plurality of cardiac signals.

Exemplary method 200 depicted in FIG. 4 may be used to determine onsets and offsets of QRS complexes from a plurality of cardiac signals. The exemplary method 200 may be generally described to be used in the evaluation of a patient's cardiac health and/or cardiac therapy being delivered to the patient.

The exemplary method 200 may include monitoring, or measuring, electrical activity using a plurality of electrodes 202. As described herein, the plurality of electrodes may include external, surface electrodes coupled to, or attached, to patient's skin, e.g., using the apparatus and systems described herein with respect to FIGS. 1-3. Additionally, the plurality of electrodes may include implantable electrodes implanted in one or more locations with a patient, e.g., using the apparatus and systems described herein with respect to FIGS. 19-21. Still further, the plurality of electrodes may further include temporarily-implanted (e.g., non-permanent, not long term, etc.) electrodes such as, e.g., electrodes located in the cavity of a patient's heart using basket catheter or the like, electrodes located outside the heart but around the heart (e.g., epicardial space) using a "sock mapping" tool or the like. Further the electrodes, or electrode apparatus, may include a mix, or combination, of external and implanted electrodes. Regardless of the electrode apparatus utilized, the exemplary method 200 includes monitoring electrical activity, and more specifically, cardiac signals or ECG signals, from at least two electrodes or channels. In other words, electrical signals maybe collected from multiple (n) electrodes such as, e.g., body surface electrodes.

Figure 6:
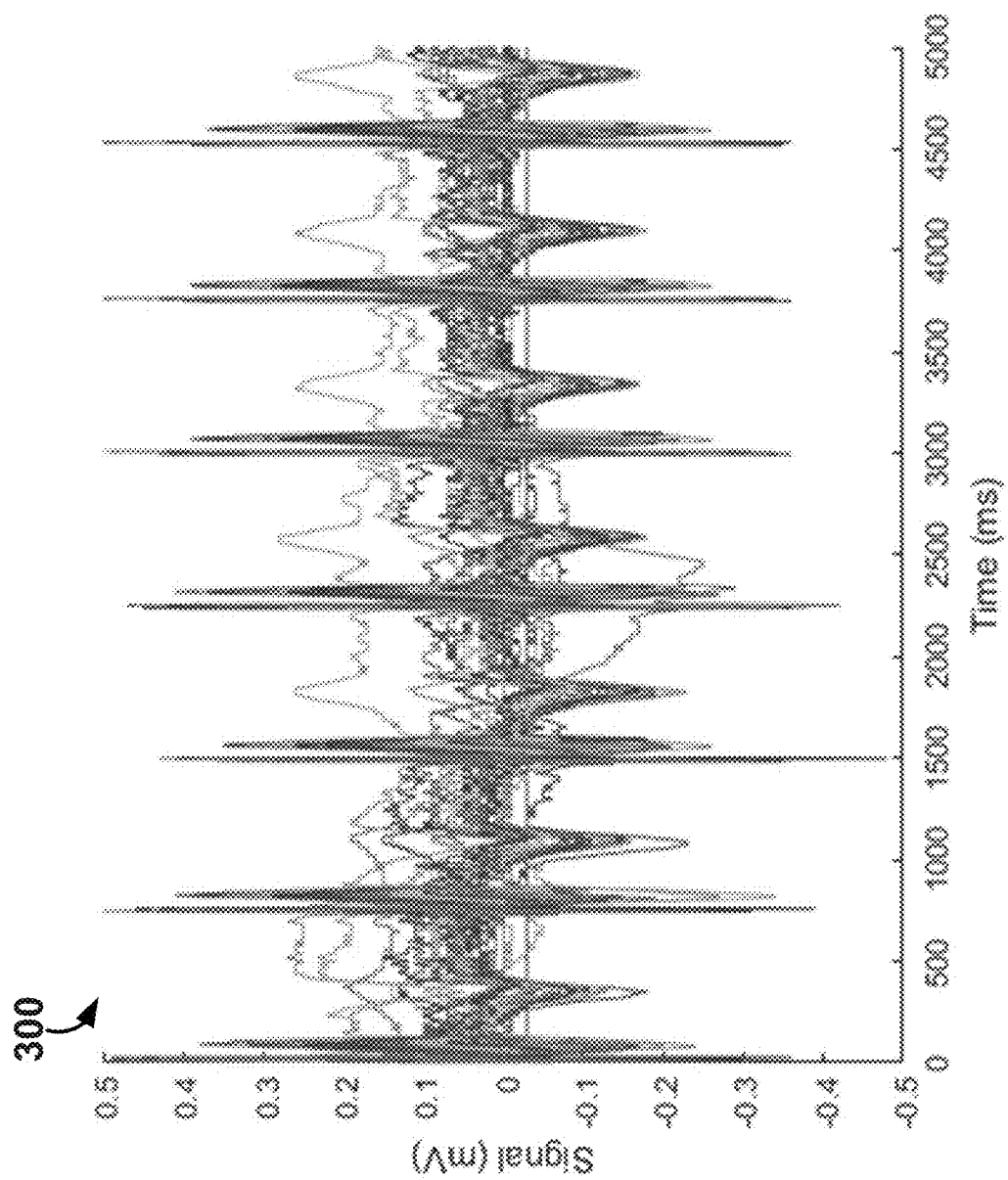
FIG. 6 is an exemplary graph of a plurality of cardiac signals monitored from surface electrodes.

An exemplary graph of a plurality of cardiac signals 300 (e.g., voltage signals measured in millivolts) monitored from surface electrodes is depicted in FIG. 6. The plurality of cardiac signals 300, as shown, were monitored over a time period of at least 5000 milliseconds. Each line represents a different cardiac signal of the plurality of signals. As shown, there are 37 signals (n=37) 302.

Figure 7:
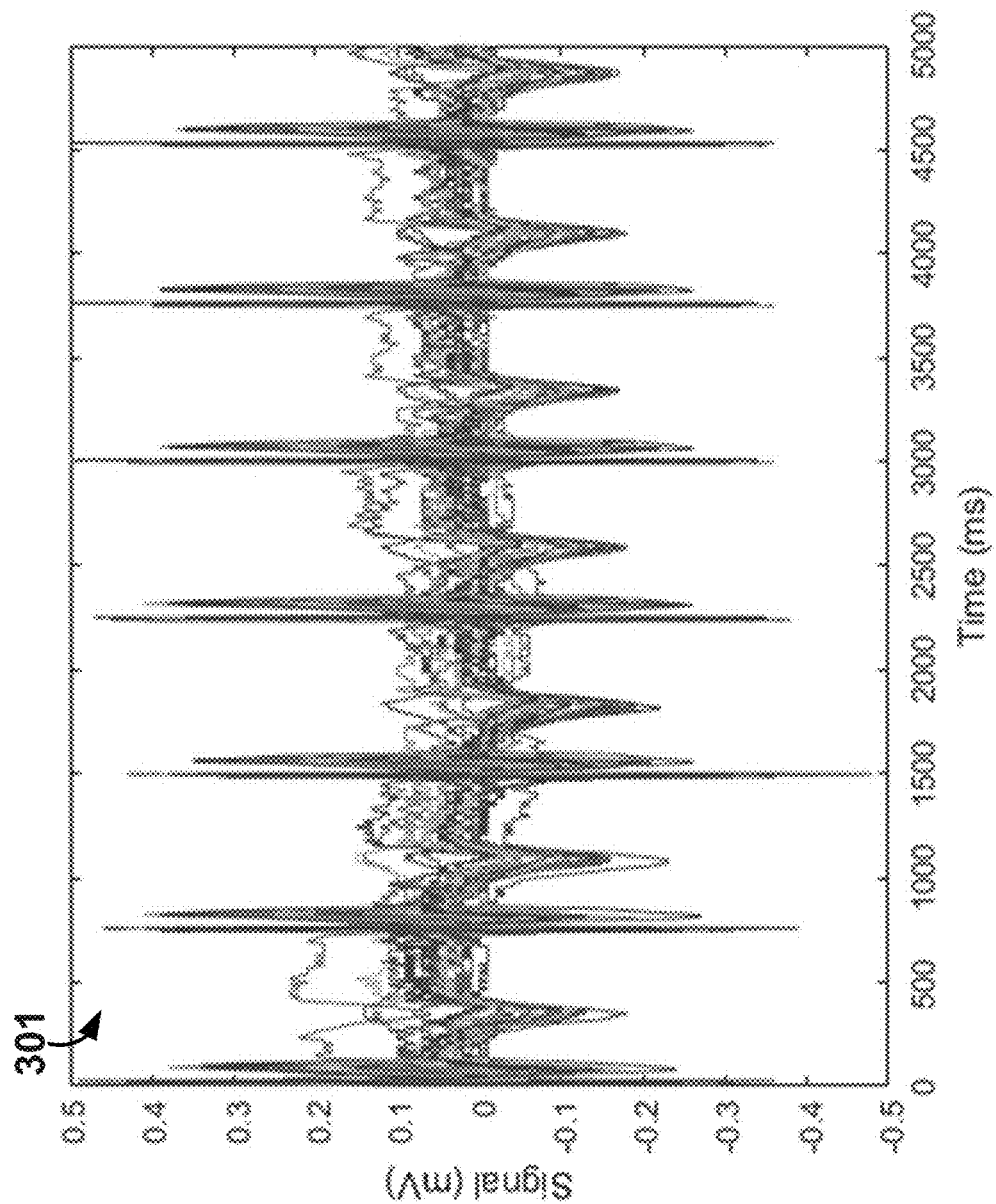
FIG. 7 is an exemplary graph of a subset of the plurality of cardiac signals of FIG. 6.

In one or more embodiments, not all of the cardiac signals monitored 202 may be used by the remainder of the exemplary method 200. For example, two or more cardiac signals may be selected from the plurality of cardiac signals to be further used by the method 200. An exemplary graph of a subset of signals 301 of the plurality of cardiac signals 301 of FIG. 6 is depicted in FIG. 7. As shown, there are 32 signals (n=32) 301.

In one or more embodiments, the exemplary method 200 may filter, or remove, one or more cardiac signals from the plurality of cardiac signals monitored 204. In other words, one or more noisy cardiac signals may be removed from the plurality of cardiac signals. The one or more noisy cardiac signals may be identified by identifying cardiac signals including, or defining, absolute areas-under-the-curve greater than or equal to a pre-filter threshold value.

Figure 8:
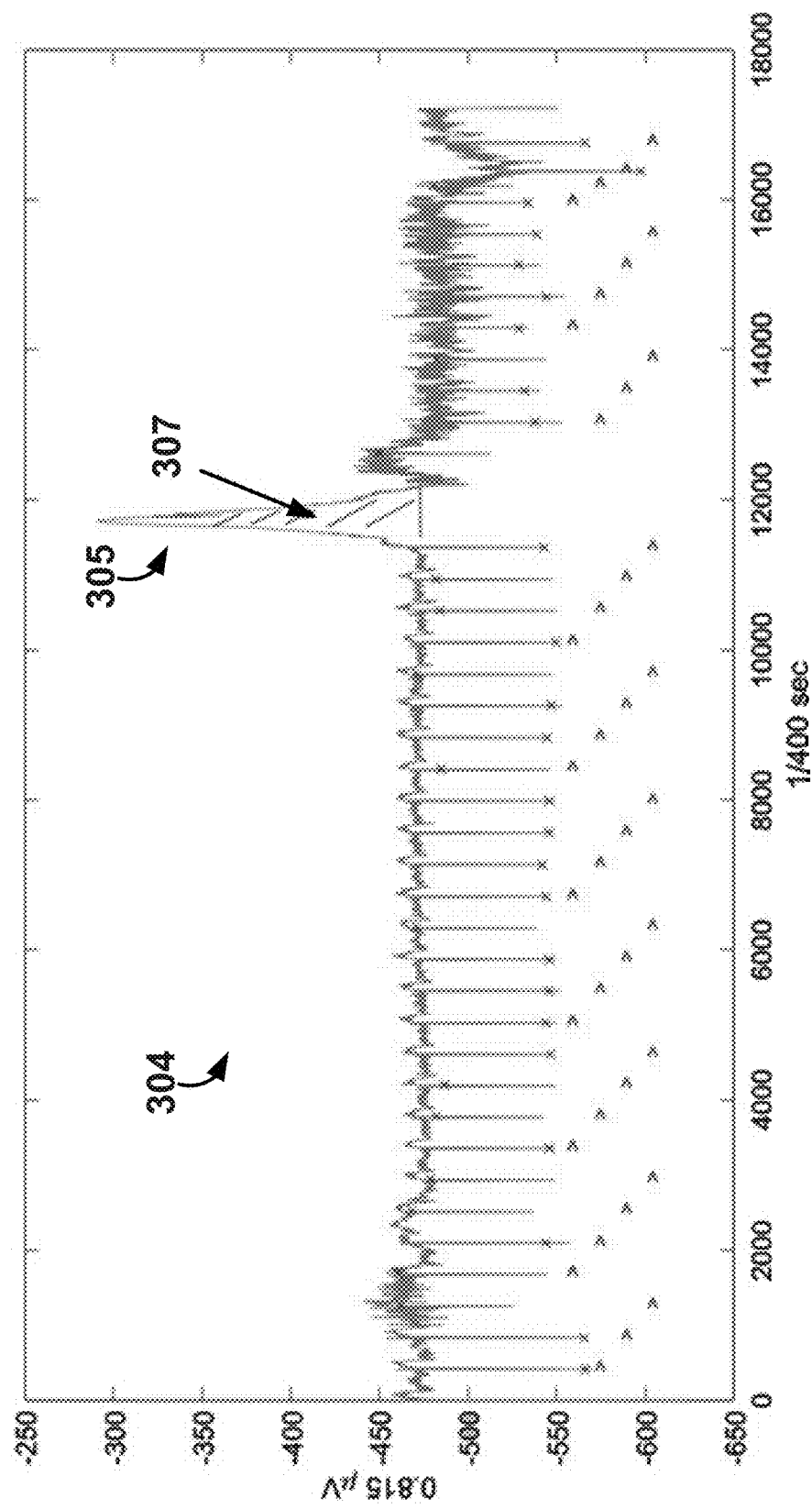
FIG. 8 is an exemplary graph of a cardiac signal including low frequency noise.

An exemplary graph of a cardiac signal 304 including low frequency noise is depicted in FIG. 8. The graph depicts a common ECG artifact 305, which may be referred to as low frequency noise. This type of noise may be observed in subcutaneous and cutaneous ECG recording devices such as, e.g., an implanted monitoring device and/or external electrode apparatus. Temporary and/or slight contact problems (e.g., electrodes in contact with tissue) may cause, or generate, a low frequency baseline drift, which, in turn, may cause R-wave sensing processes, or algorithms, to detect the noise as an R-wave and/or fail to sense the following two or three R-waves because, e.g., the noise may be larger than the subsequent R-waves. The exemplary methods and systems described herein may detect the low frequency noise 305 so as to be able to reject, or filter, this type of noise from the plurality of cardiac signals being monitored.

The exemplary method 200 may filter 204 the plurality of signals using area-under-curve (AUC) to detect the low frequency noise, such that, e.g., when the noise is detected, the monitoring apparatus may stop monitoring, or recording, cardiac signals at least temporality. More specifically, the filter 204 may evaluate the AUC for a selected portion of the cardiac signal and may determine whether the AUC of the selected portion is greater than a threshold value, which may be determined by all of the signal data within the selected portion.

For example, the AUC 307 of the noise artifact 305 is greater than a threshold AUC value (e.g., a baseline voltage-time value). A first moving window, or selected portion, may be used, which may be about 0.01 to about 3 seconds long prior to the current time point. A baseline signal value (e.g., voltage) may be determined based on the signal within the first moving window, or selected portion. The threshold value may be a median, mean, or other statistic metric of the AUC measurements within in the moving window or selected portion.

In one embodiment, the AUC 307 of the signal within a second moving window, or selected portion, (e.g., voltage) after the current time point may be calculated. Then calculate the AUC by subtracting the baseline values from the first moving window from the values in the second moving window (e.g., AUC=EGM voltages in the second window—baseline EGM voltages in the first window). As shown in FIG. 8, the AUC 307 of the low frequency noise 305 may be several times higher than the AUC of typical R-waves or T-waves.

In another embodiment, a single window up to 5 seconds long of the signal may be evaluated. The AUC 307 may be determined, or calculated, for each signal within this window with opportunity to subtract baseline ECG signal value if desired. A threshold may be selected relative to some statistic of the AUC (e.g., 3 times the median AUC in this window). The signals above the threshold may be removed or "filtered out."

Additionally, the same filtering 204 of the plurality of signals 310 using area-under-curve (AUC) to detect the low frequency noise is depicted in FIG. 9 to, e.g., remove signals monitored using external electrodes having to detached or loosely coupled electrodes to improve R-wave timing accuracy. More specifically, an exemplary graph of a plurality of cardiac signals 310 prior to such filtering 204 and an exemplary graph of a dispersion signal 314 overlaid over the plurality of cardiac signals 312 after such filtering 204 are depicted in FIG. 9. As shown, one or more cardiac signals were removed, or filtered, from the first, or top, graph ("Before Filtering") to the second, or bottom, graph ("After Filtering"), which may result a better dispersion signal describe further herein and better identification of peak, or maximum, values associated with, or corresponding, to R-waves of QRS complexes within the plurality of cardiac signals.

The exemplary method 200 may further include generating a dispersion signal 206 from the plurality of cardiac signals monitored 202 and potentially filtered 204. The dispersion signal may be representative of the dispersion of the plurality of cardiac signals over time. The dispersion signal may be the standard deviation of the plurality of cardiac signals over time. In other embodiments, the dispersion signal may be variance, a coefficient of variance, range, mean absolute deviation, a measure of central tendency (e.g., like the mean), interquartile deviation of amplitudes, median absolute deviation taken about a measure of central tendency like the mean, median, mode, and/or another statistical measure of the plurality of cardiac signals over time.

Figure 10:
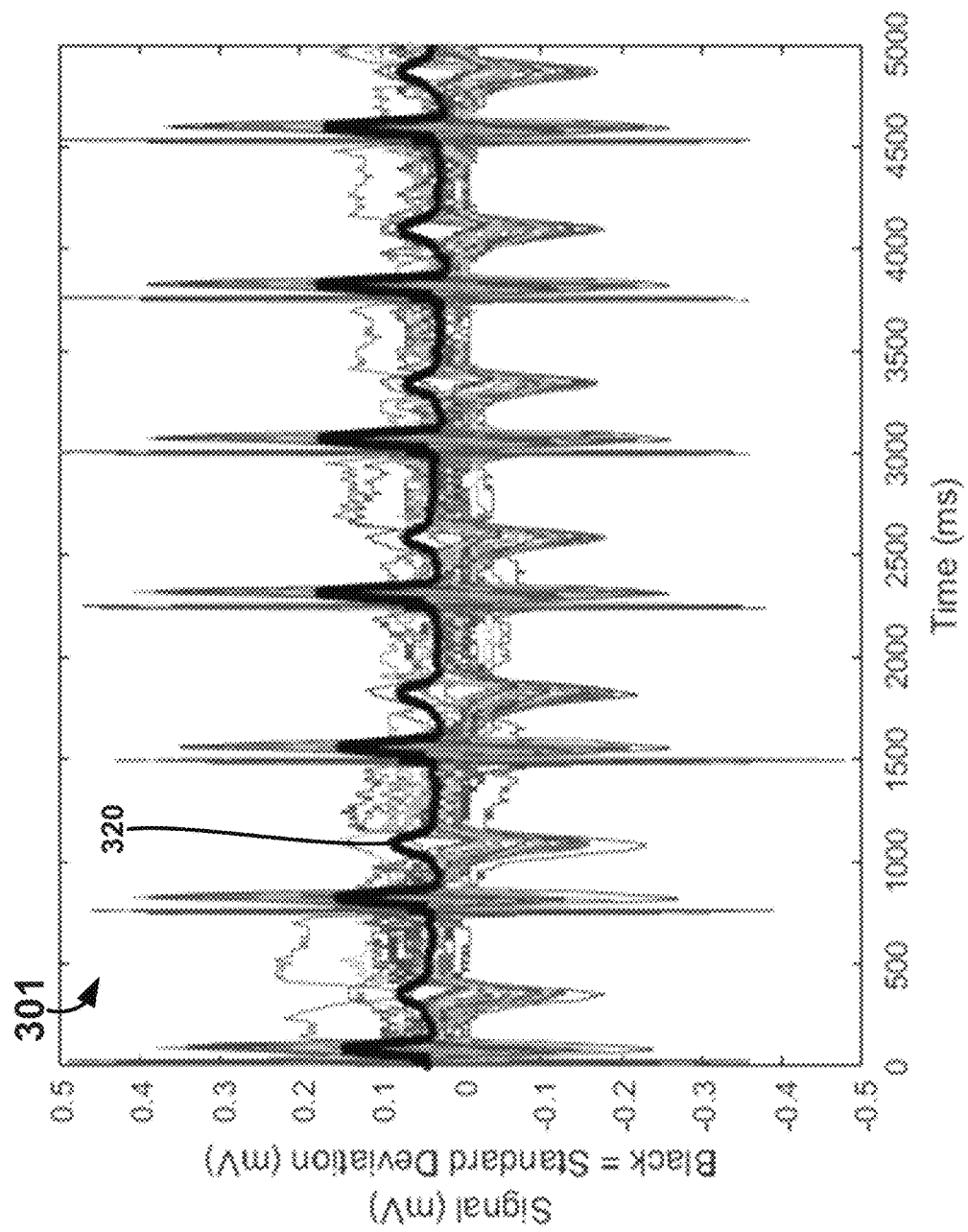
FIG. 10 is an exemplary graph of a dispersion signal overlaid over the subset of the plurality of cardiac signals of FIG. 7.

An exemplary graph of a dispersion signal 320 overlaid over the subset of the plurality of cardiac signals 301 of FIG. 7 is depicted in FIG. 10. The standard deviation across all signals 301 in the subset at each time point was calculated to generate the dispersion signal 320. As shown, the thin lines are the signals from the subset 301, and the thick black line is the dispersion signal 320 (e.g., a standard deviation) that was calculated across all signals at each time point.

Figure 11:
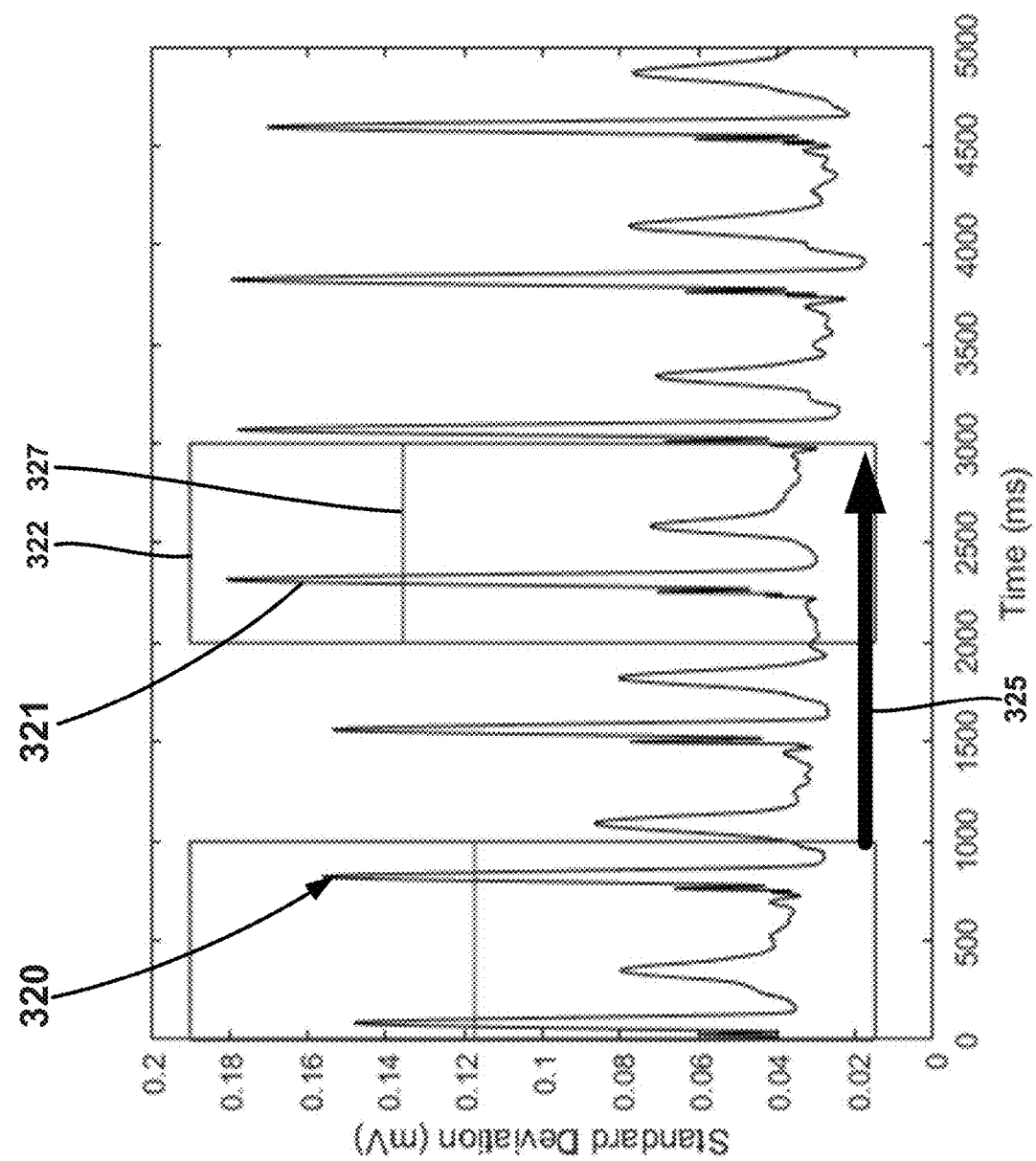
FIG. 11 is an exemplary graph of the dispersion signal of FIG. 10.

An exemplary expanded graph of the dispersion signal 320 of FIG. 10 without the plurality of cardiac signals 301 is depicted in FIG. 11, which will be further described herein with reference to the user of the dispersion signal 320.

The dispersion signal may be used by the method 200 to determine a QRS onset time value and a QRS offset time value 208 for each of at least one QRS complex within the monitored electrical activity 202 based on the generated dispersion signal 206. In other words, the generated dispersion signal may be used to determine onset time value and a QRS offset time value 208, which may be later used to conduct various measurements such as, e.g., activation time measurements, using the plurality of monitored cardiac signals. The QRS onset time value may be described as a time value, or point in time, that is indicative of the start, or beginning, of the QRS complex of the cardiac signals when taking into consideration the plurality of monitored cardiac signals. The QRS offset time value may be described as a time value, or point in time, that is indicative of the end of the QRS complex of the cardiac signals when taking into consideration the plurality of monitored cardiac signals. The QRS onset and offset time values may be used to calculate one or more values or metrics from or using the plurality of cardiac signals as will be described further herein.

Figure 5:
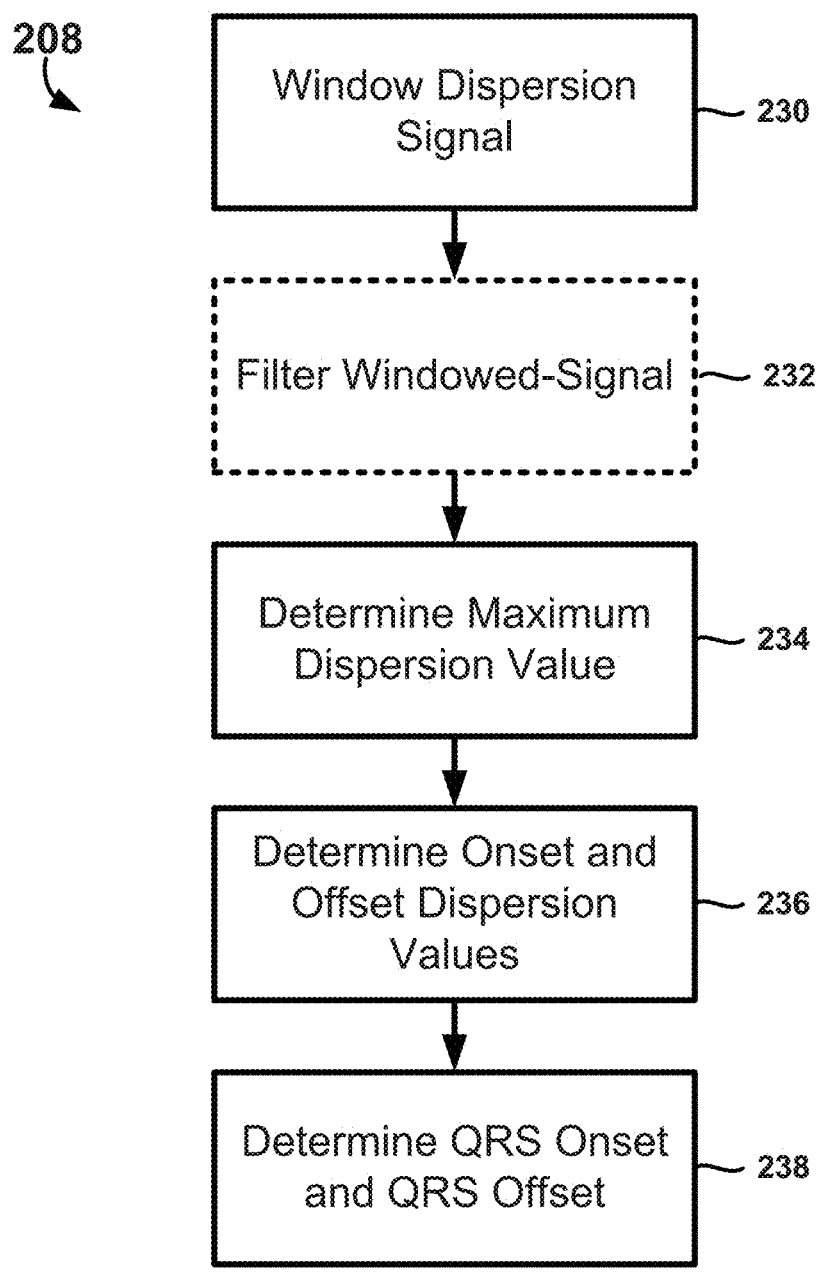
FIG. 5 is a more detailed block diagram of determining QRS duration from a dispersion signal of FIG. 4.

Determination of the QRS onset time value and the QRS offset time value 208 is further depicted in the flow diagram of FIG. 5. As shown, determination of the QRS onset time value and the QRS offset time value 208 may include windowing the dispersion signal 230, filtering the windowed signal 232, determining a maximum dispersion value 234, determining a minimum dispersion values 236 about the maximum dispersion value, and determining the QRS onset time value and the QRS offset time value using the onset and offset dispersion values about the maximum dispersion value 238 (e.g., the onset and offset dispersion values may be related to the minimum dispersion values about the maximum dispersion value 238 such as a percentage thereof).

Determination of the QRS onset time value and the QRS offset time value 208 may be begin may selecting a portion 321 of the dispersion signal 320 over a selected time period 322. The selected time period 322 may be described as a moving time window, which may move along (representative by arrow 325) along the dispersion signal 320 such that the analysis may be performed along the dispersion signal 320 in discrete slices or portions 321 of the dispersion signal 320. The QRS onset and offset time values for each QRS complex may be determined, or identified, within the monitored electrical activity of the selected time period 322 based on the selected portion 321 of the dispersion signal 320.

The selected time period, or moving time window, may be less than or equal to about 5 seconds. In other embodiments, the selected time period, or moving time window, may be less than or equal to about 4.5 seconds, less than or equal to about 4 seconds, less than or equal to about 3.5 seconds, less than or equal to about 3 seconds, less than or equal to about 2.5 seconds, less than or equal to about 2 seconds, less than or equal to about 1 second, etc. and/or greater than or equal to about 0.25 seconds, greater than or equal to about 0.5 seconds, greater than or equal to about 1.25 seconds, greater than or equal to about 2.75 seconds, greater than or equal to about 3.25 seconds, greater than or equal to about 3.75 seconds, greater than or equal to about 4.25 second, etc. Further, in one or more embodiments, the selected time period, or moving time window, may be selected, or adjusted, based on the patient's heart rate so as to capture, e.g., one QRS complex per selected time period, two or more QRS complexes per selected time period, etc. In at least one embodiment, the selected time period, or moving time window, may be defined to capture a single QRS complex in most instances.

In the example depicted in FIG. 11, a 1000 millisecond selected time period, or moving time window, 322 is used that shifts (represented by arrow 325) as individual dispersion values are evaluated.

Prior to determining a maximum dispersion value within the selected time period 322, the exemplary method 208 may selectively filter the windowed signal 232 using one or more filtering techniques or processes to, e.g., avoid signal artifacts that do not correspond to the QRS complex such as the P-wave. the T-wave, and noise. To do so, in one embodiment, a threshold value 327 may be determined, and only the dispersion values greater than threshold value 327 may be considered when determining a maximum dispersion value within the selected time period 322. As shown in FIG. 11, the threshold value is represented by the horizontal line 327 within the selected time period 322. The threshold value may be based one or more statistics or metrics designed to allow peak, or maximum, dispersion values to remain while eliminating dispersion values that may not be relevant when identifying peak, or maximum, values. The threshold value may be based on, or defined by, a selected percentage of the maximum dispersion value of the dispersion signal 320. In other words, the dispersion signal may be filtered 232 to remove one or more values of the dispersion signal 320 that are less than or equal to a selected percentage of the maximum dispersion value of the dispersion signal. The selected percentage may be greater than or equal to about 50%, greater than or equal to about 65%, greater than or equal to about 75%, greater than or equal to about 85%, etc. and/or less than or equal to about 90%, less than or equal to about 80%, less than or equal to about 70%, less than or equal to about 60%, etc.

In other embodiments, high pass filtering may be used to filter the dispersion signal 320 to remove one or more dispersion values of the dispersion signal corresponding to at least one of a T-wave and a P-wave in the plurality of cardiac signals. Further, the filtering the plurality of cardiac signals through a filter (e.g., high-pass) may to remove the lower frequency components like P- and T-waves, while preserving the higher frequency QRS. Additional illustrative filtering processes that may be used with the illustrative systems and methods described herein may be described in U.S. patent application Ser. No. 15/802,615 entitled "Detection of Noise Signals in Cardiac Signals" and filed on Nov. 3, 2017, which is incorporated by reference herein in its entirety.

Figure 12:
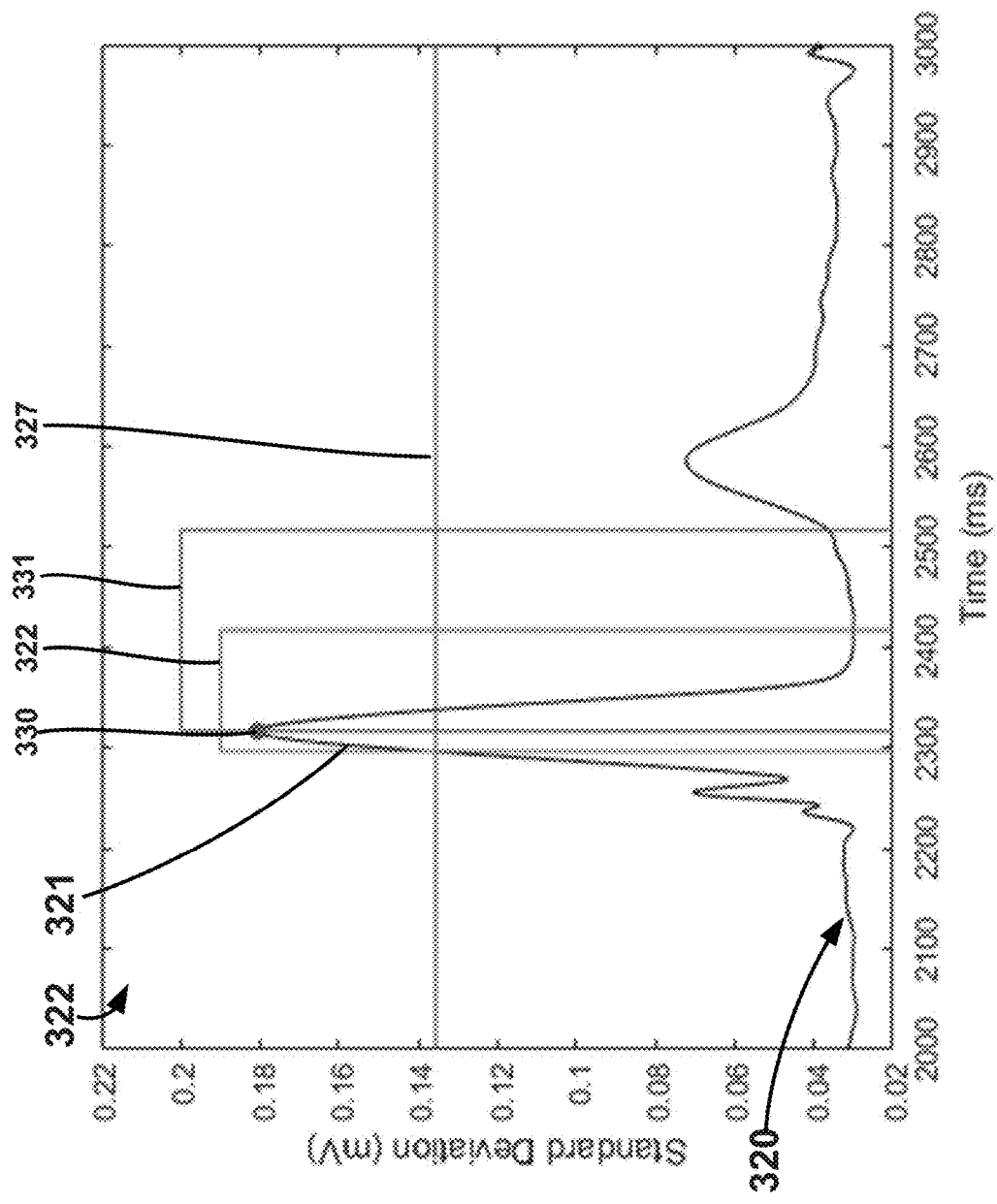
FIG. 12 is an exemplary graph of a portion of the dispersion signal of FIG. 11 including identification of a maximum, or peak, dispersion value.

For use in determining QRS onset and offset time values 208, a maximum dispersion value may be determined 234 within the selected time period 322. An exemplary graph of the selected portion 321 of the dispersion signal 320 of FIG. 11 within the selected time period 322 is depicted in FIG. 12. In this embodiment, the maximum dispersion value 330 may be determined by analyzing each of the dispersion values after the first dispersion value exceeds the threshold 327 for a selected time period. In other embodiments, all dispersion values over the threshold 327 may be evaluated. As show, the selected time period is 120 milliseconds. In another embodiment, the selected time period may be 200 milliseconds. In other embodiments, the selected time period may be greater than or equal to about 80 milliseconds (ms), greater than or equal to about 100 ms, greater than or equal to about 140 ms, greater than or equal to about 160 ms, greater than or equal to about 180 ms, greater than or equal to about 220 ms, greater than or equal to about 240 ms, etc. and/or less than or equal to about 250 ms, less than or equal to about 230 ms, less than or equal to about 210 ms, less than or equal to about 190 ms, less than or equal to about 150 ms, less than or equal to about 130 ms, etc.

As shown, the maximum dispersion value 330 is determined. Additionally, as shown, a blanking period 331 extends for a selected blanking time period beyond the determined maximum dispersion value 330, within which no further peak, or maximum, dispersion values will be identified (e.g., to avoid noise, T-waves, etc.). In this example, the blanking time period 321 is 200 milliseconds. In other embodiments, the blanking time period 321 may be greater than or equal to about 50 milliseconds, greater than or equal to about 150 milliseconds, greater than or equal to about 300 milliseconds, greater than or equal to about 400 milliseconds, etc. and/or less than or equal to about 500 milliseconds, less than or equal to about 350 milliseconds, less than or equal to about 250 milliseconds, less than or equal to about 100 milliseconds, etc.

After the maximum, or peak, dispersion value 330 is determined 234, onset and offset dispersion values 236 may be determined proximate the maximum dispersion value 330, which may be used to determine QRS onset and offset time values. For example, an onset dispersion value 332 may be determined for the QRS onset time value, and an offset dispersion value 334 may be determined for the QRS offset time value. The onset dispersion value 332 corresponding to the QRS onset time value may occur prior to the maximum dispersion value 330, and the offset dispersion value 334 corresponding to the QRS offset time value may occur after the maximum dispersion value 330.

Figure 13:
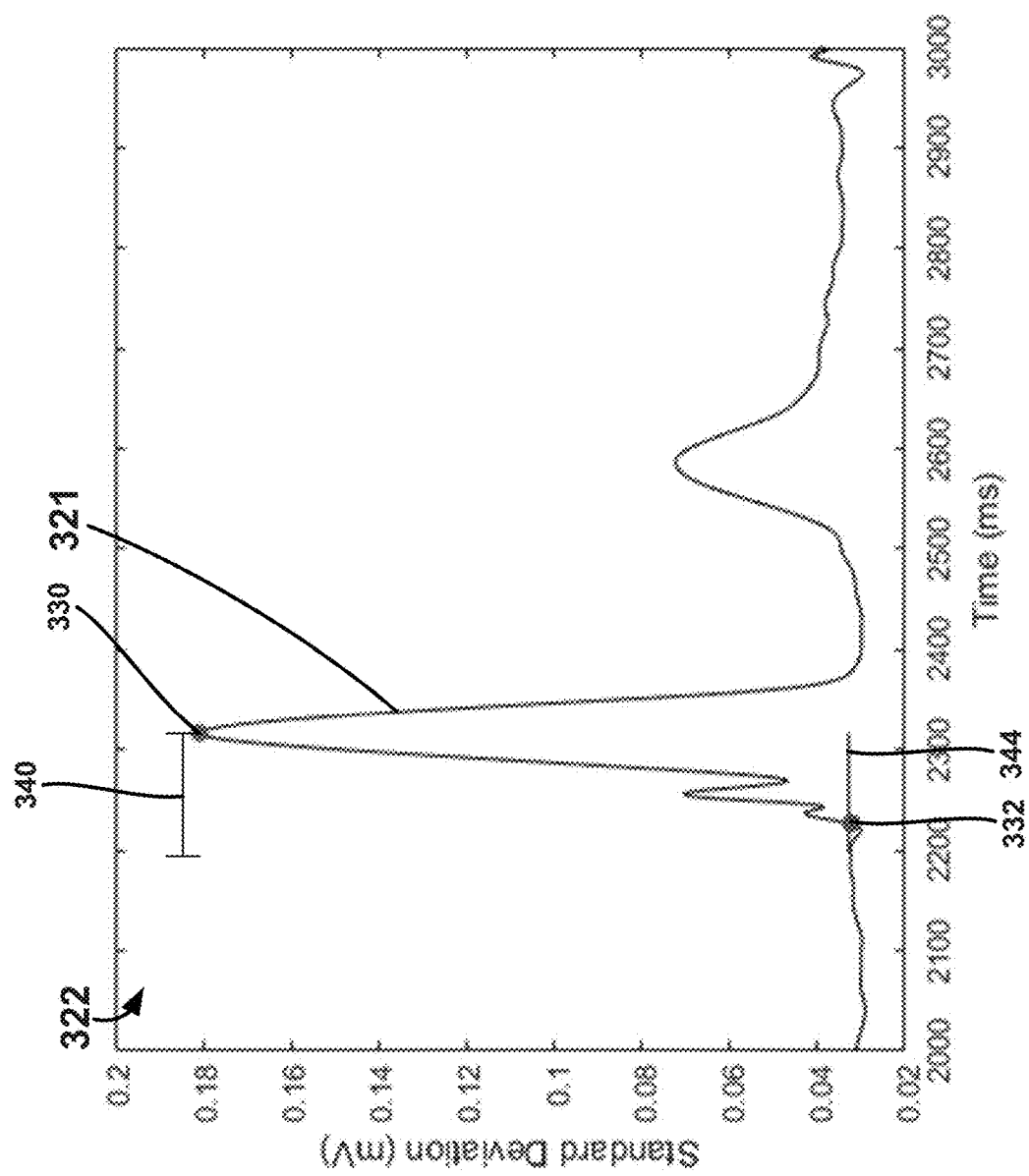
FIG. 13 is the exemplary graph of the portion of the dispersion signal of FIG. 12 including identification of an onset dispersion value prior to the maximum value corresponding to the onset, or onset time value, of the QRS duration.
Figure 14:
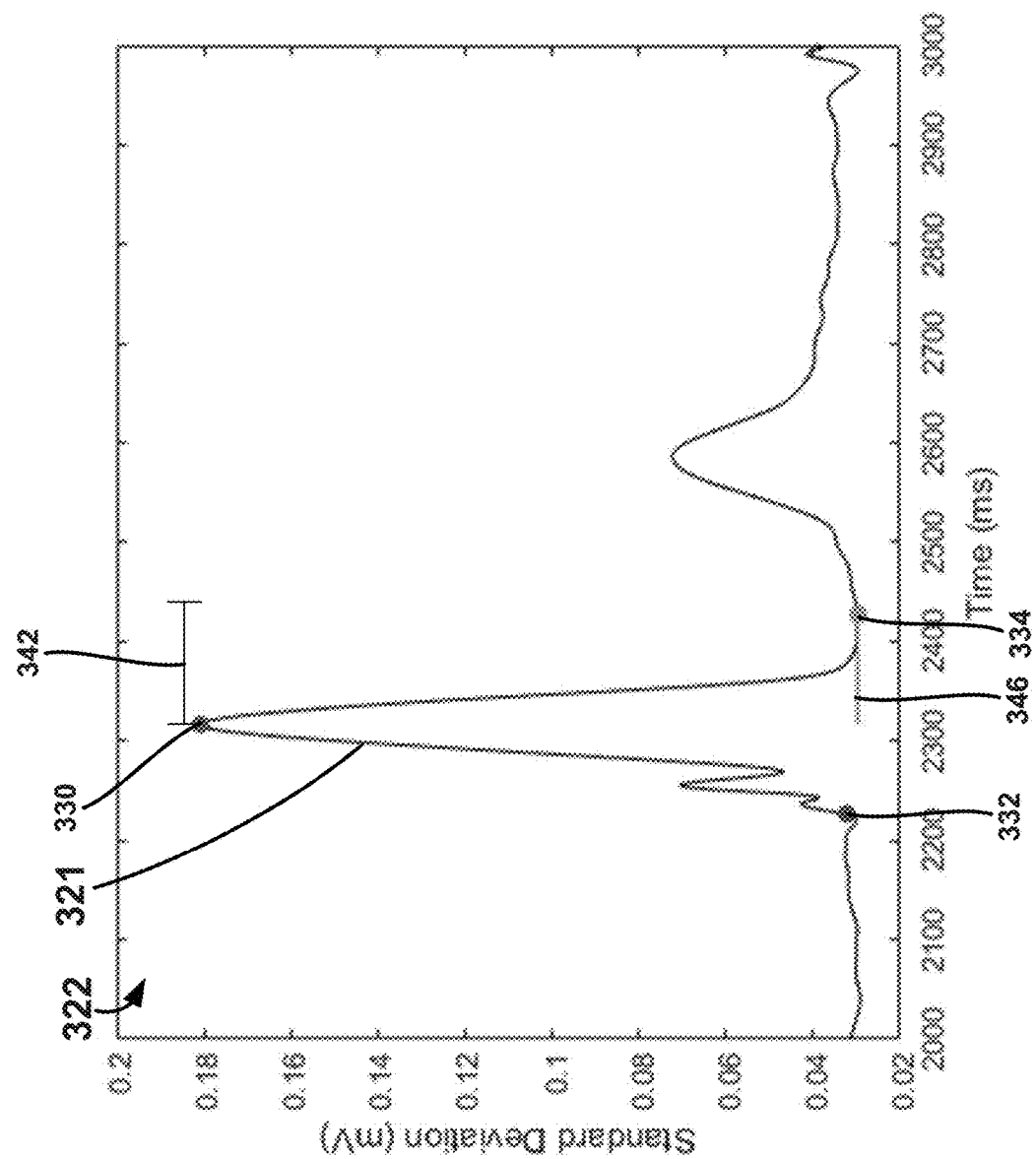
FIG. 14 is the exemplary graph of the portion of the dispersion signal of FIG. 12 including identification of an offset dispersion value after the maximum value corresponding to the offset, or offset time value, of the QRS duration.

In one or more embodiments, the onset dispersion value 332 of the dispersion signal 320 corresponding to the QRS onset time value may be determined within a first time period 340 before the maximum dispersion value 330 of the dispersion signal 320 as shown in FIG. 13. Likewise, the offset dispersion value 334 of the dispersion signal 320 corresponding to the QRS offset time value may be determined within a second time period 342 after, or following, the maximum dispersion value 330 of the dispersion signal 320 as shown in FIG. 14.

The onset and offset dispersion values prior to and occurring after the maximum dispersion value 330 that is within 10%, 20%, 30%, 40%, 50%, 60%, or another selected percentage or statistical metric, of the minimum dispersion values within the first and second time periods 340, 342, respectively, may be used to determine QRS onset and offset time values. For example, the onset dispersion value 332 may be the latest dispersion value of the dispersion signal 320 within the first time period 340 before a maximum dispersion value 330 of the dispersion signal 320 that is less than or equal to 110% of a minimum dispersion value of the dispersion signal 320 within the first time period 322 may be used to determine the QRS onset time value. Further, the offset dispersion value 324 may be the earliest dispersion value of the dispersion signal 320 within the second time period 342 after the maximum dispersion value 330 of the dispersion signal 320 that is less than or equal to 110% of a minimum dispersion value of the dispersion signal 320 within the second time period 342. The horizontal line 344 represents 10% greater than the minimum dispersion value within the first time period 340, and the horizontal line 346 represents 10% greater than the minimum dispersion value within the second time period 342.

In another embodiment, the minimum dispersion values within the first and second time periods 340, 342, may be used as the onset and offset dispersion values respectively.

The onset and offset dispersion values 332, 334 may be used to determine the QRS onset and offset time values, respectively, 238 because the time values at which the onset and offset dispersion values 332, 334 occur within the first and second time periods 340, 342 may be the QRS onset and QRS offset time values, respectively. In other words, the time at which the onset dispersion value 332 occurs is the QRS onset time value, and the time at which the offset dispersion values 334 occurs is the QRS offset time value.

Figure 15:
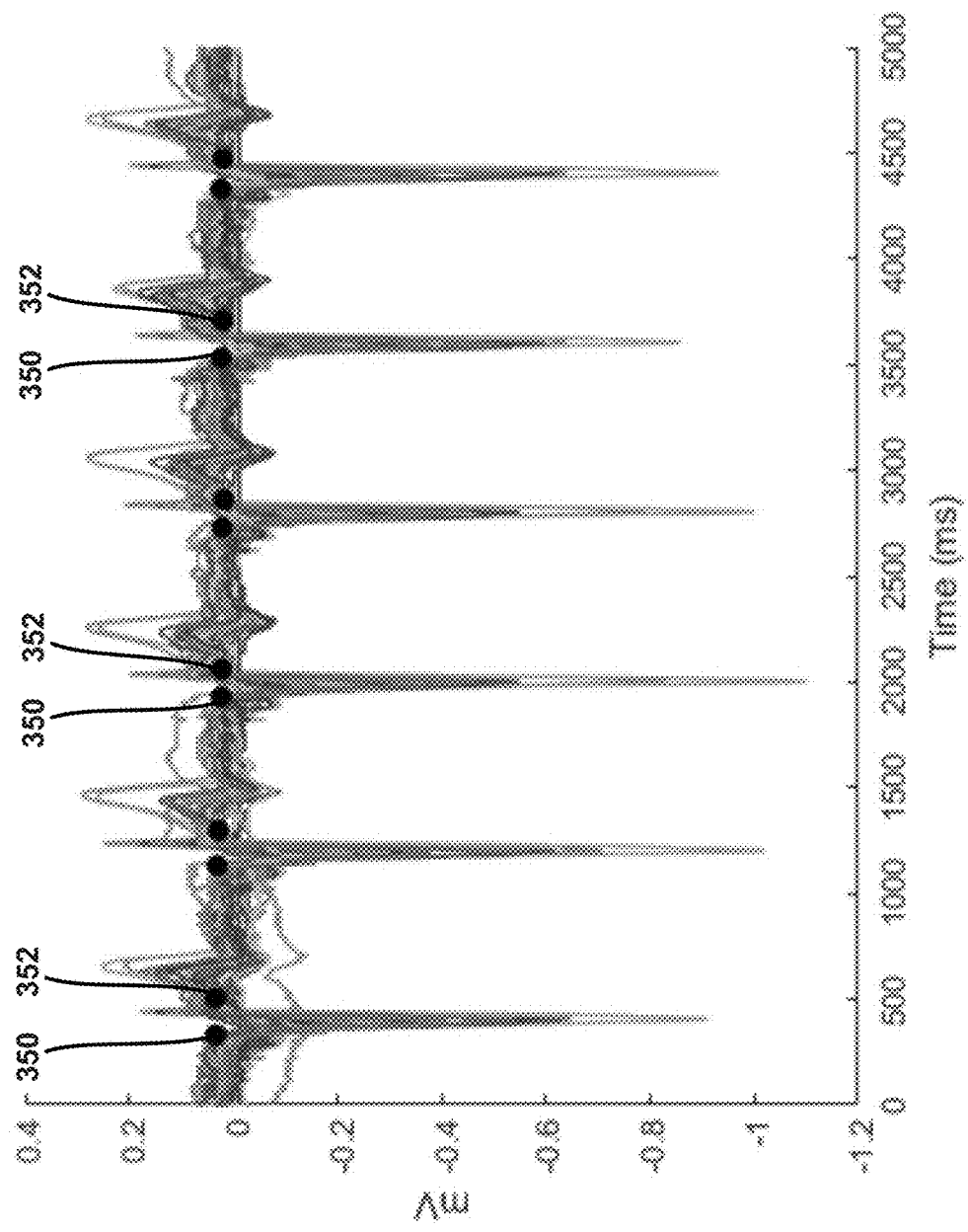
FIG. 15 is an exemplary graph of a plurality of cardiac signals including a plurality of QRS complexes and identified QRS onsets and offsets using the exemplary methods and systems described herein.
Figure 16:
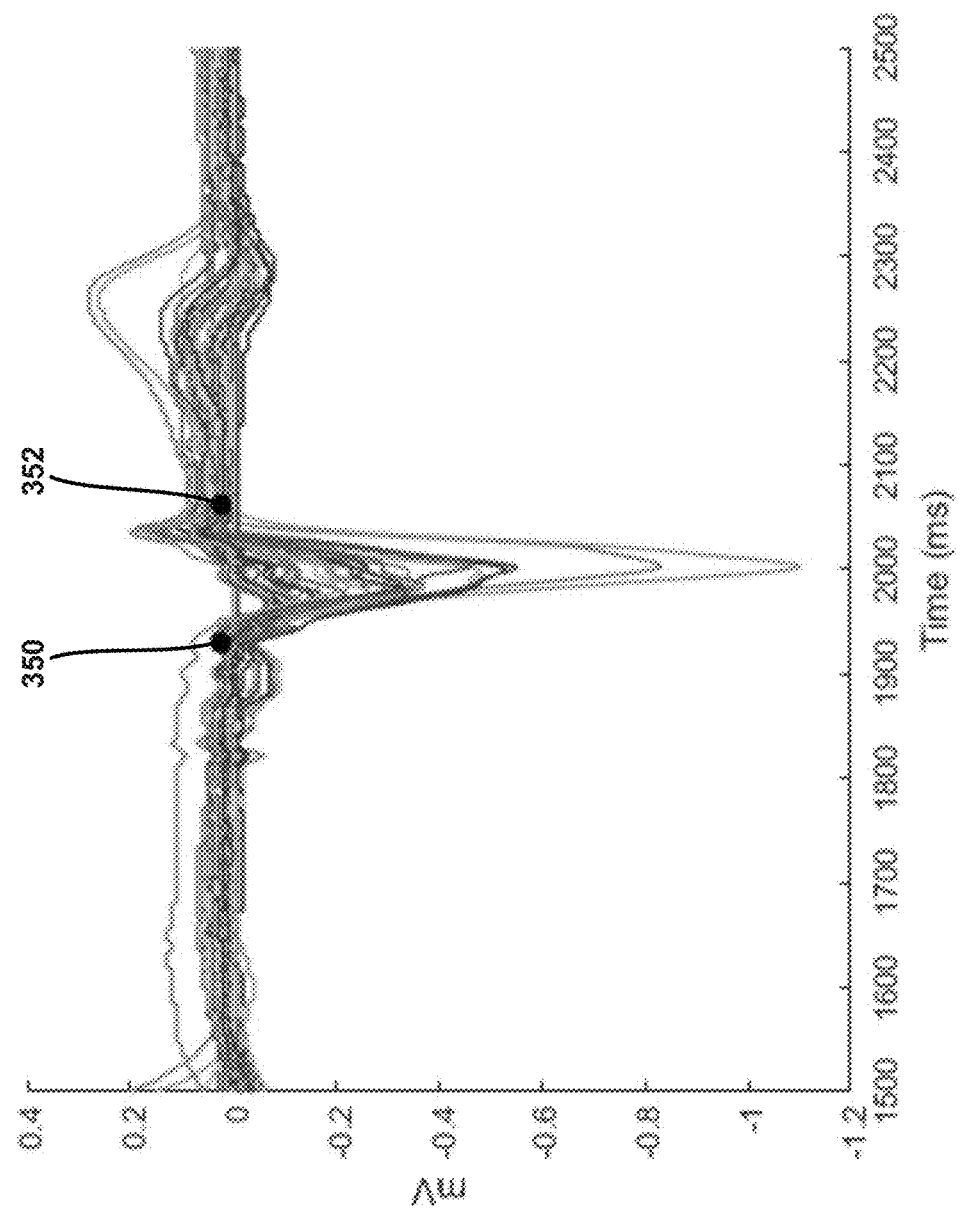
FIG. 16 is an exemplary graph of a plurality of cardiac signals including a single QRS complex, an identified QRS onset, and an identified offset using the exemplary methods and systems described herein.

An exemplary graph of a plurality of cardiac signals including a plurality of QRS complexes and identified QRS onset time values 350 and offset time values 352 using the exemplary methods and systems described herein is depicted in FIG. 15, and an exemplary graph of a plurality of cardiac signals including a single QRS complex, an identified QRS onset time value 350, and an identified QRS offset time value 352 using the exemplary methods and systems described herein is depicted in FIG. 16.

The QRS onset and offset time values may be used to determine activations times with each of the QRS complexes of each of the plurality of cardiac signals 212. More specifically, activation times can be determined using one or more fiducial points within the QRS duration defined by the QRS onset time value and the QRS offset time value of each of the plurality of cardiac signals using the systems, methods, and processes described herein with respect to FIGS. 1-3.

Prior to determining activation times 212 based on the cardiac signal and the QRS onset and offset time values, noisy signals may be filtered 210 based on one or more metrics or statistics corresponding to the cardiac signal values between the QRS onset time value and the QRS offset time value within each of the plurality of cardiac signals. For example, an absolute amplitude may be determined between the QRS onset time value and the QRS offset time value for each of the QRS complexes for each of the plurality of cardiac signals, and one or more cardiac signals of the plurality of cardiac signals may be selected, or filtered, based on the absolute amplitude. More specifically, in at least one embodiment, selecting one or more cardiac signals of the plurality of cardiac signals may define an absolute amplitude greater than or equal to a threshold value, and the threshold value is less than the median absolute amplitude of the plurality of cardiac signals. Then, the activation times may be generated based on the selected, or filtered, one or more cardiac signals.

One or more metrics such as metrics of electrical and mechanical cardiac heterogeneity may be generated 214 based on the activation times. Electrical heterogeneity information and other cardiac therapy information may be described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety.

Electrical heterogeneity information may be defined as information indicative of at least one of mechanical synchrony or dyssynchrony of the heart and/or electrical synchrony or dyssynchrony of the heart. In other words, electrical heterogeneity information may represent a surrogate of actual mechanical and/or electrical functionality. In at least one embodiment, electrical heterogeneity information may be used to determine a surrogate value representative of the maximum left ventricular pressure rate. The left ventricular pressure may be typically monitored invasively with a pressure sensor located in the left ventricular of a patient's heart. As such, the use of electrical heterogeneity information to determine a surrogate value representative of the maximum left ventricular pressure rate may avoid invasive monitoring using a left ventricular pressure sensor.

In at least one embodiment, the electrical heterogeneity information may include a standard deviation of ventricular activation times corresponding to some or all of the external electrodes, e.g., of the electrode apparatus 110. Further, regional electrical heterogeneity information may include standard deviations and/or averages of activation times corresponding to electrodes located in certain anatomic areas of the torso. For example, external electrodes on the left side of the torso of a patient may be used to compute regional left electrical heterogeneity information.

The electrical heterogeneity information may be generated using one or more various systems and/or methods. Electrical heterogeneity information may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

Electrical heterogeneity information may include one or more metrics or indices. For example, one of the metrics, or indices, of electrical heterogeneity may be a standard deviation of activation-times (SDAT) measured by some or all of the electrodes on the surface of the torso of patient. In some examples, the SDAT may be calculated using the estimated cardiac activation times over the surface of a model heart.

Another metric, or index, of electrical heterogeneity may be a left standard deviation of surrogate electrical activation times (LVED) monitored by external electrodes located proximate the left side of patient. Further, another metric, or index, of electrical heterogeneity may include an average of surrogate electrical activation times (LVAT) monitored by external electrodes located proximate the left side of patient. The LVED and LVAT may be determined (e.g., calculated, computed, etc.) from electrical activity measured only by electrodes proximate the left side of the patient, which may be referred to as "left" electrodes. The left electrodes may be defined as any surface electrodes located proximate the left ventricle, which includes region to left of the patient's sternum and spine. In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Another exemplary metric, or index, of dyssynchrony may be a range of activation times (RAT) that may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another exemplary metric, or index, of electrical heterogeneity information may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The exemplary metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, additional cardiac information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Further, such additional cardiac information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZAING CRT THERAPY" and published on Apr. 16, 2009, each of which is incorporated herein by reference in its entirety.

Figure 17:
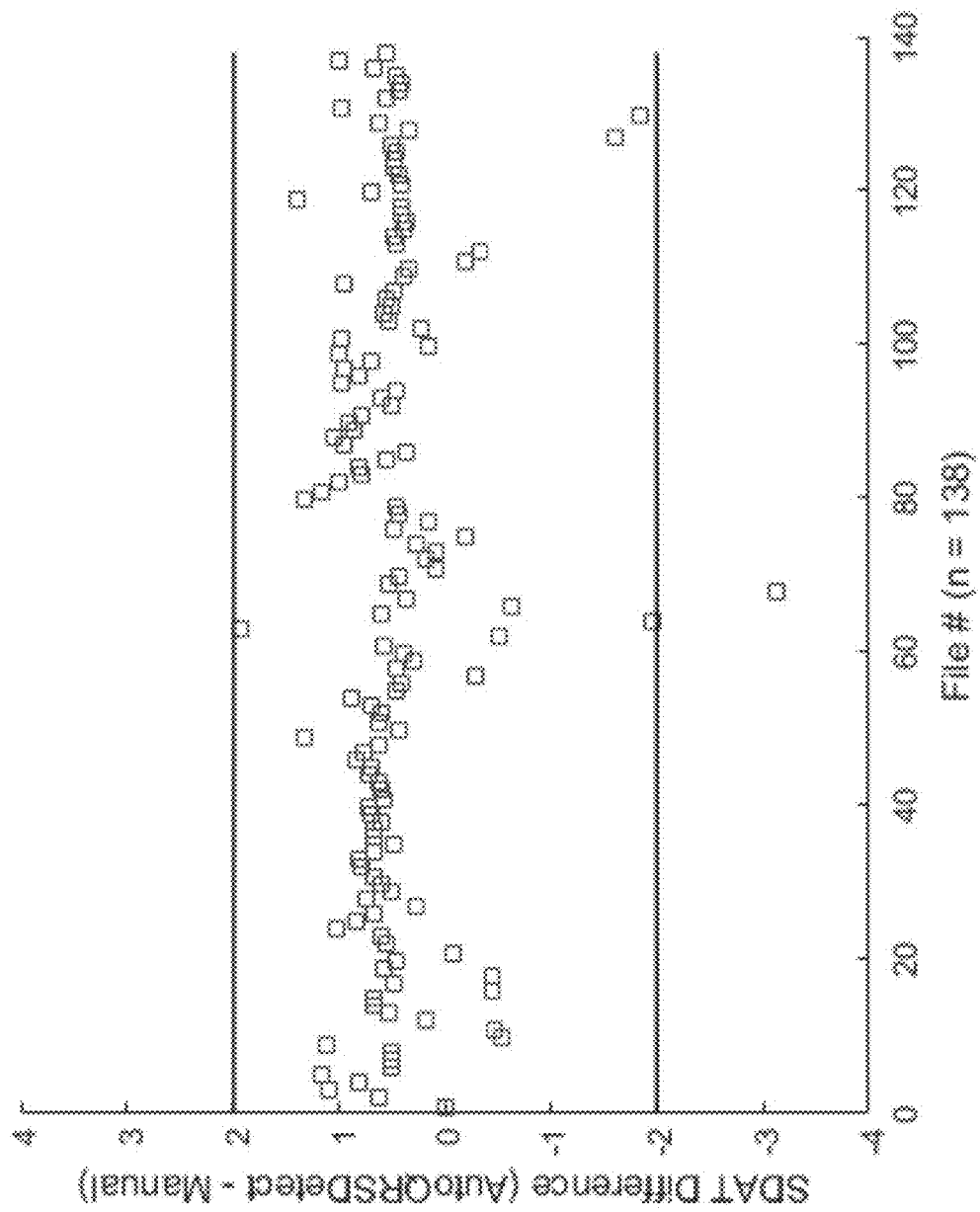
FIG. 17 is an exemplary graph of the differences of standard deviation of activation-times (SDAT) generated using manually determined QRS durations and QRS durations determined by the exemplary methods and systems described herein.
Figure 18:
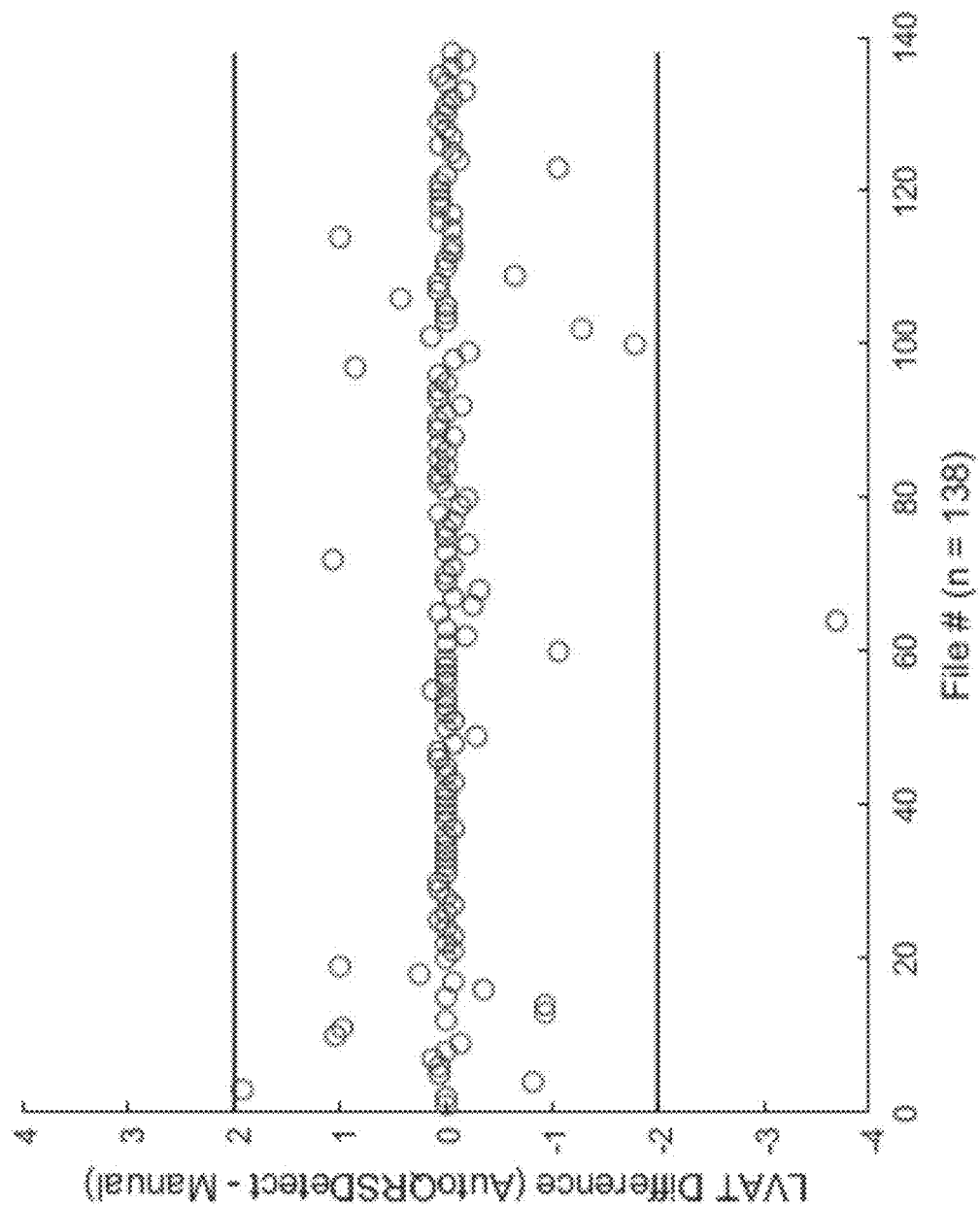
FIG. 18 is an exemplary graph of the differences of average left surrogate electrical activation times (LVAT) generated using manually determined QRS durations and QRS durations determined by the exemplary methods and systems described herein.

An exemplary graph of the differences of standard deviation of activation-times (SDAT) generated using manually determined QRS durations and QRS durations determined by the exemplary methods and systems described herein is depicted in FIG. 17. And, an exemplary graph of the differences of average left surrogate electrical activation times (LVAT) generated using manually determined QRS durations and QRS durations determined by the exemplary methods and systems described herein is depicted in FIG. 18. As shown, the exemplary systems and methods were used to provide activation times using external electrode apparatus (e.g., ECG belt) from 138 data files. SDAT and LVAT were calculated using the QRS onset and offset times values determined using the exemplary systems, methods, and processes. "Manual" measurements, where a user attempted to identify the QRS onset and offset times values "by hand" were used for comparison, and the SDAT and LVAT measurements were calculated at the time of data collection. The SDAT difference as shown equals SDAT determined using the exemplary systems and methods minus SDAT from the "manual" measurement, and the LVAT difference equals LVAT determined using the exemplary systems and methods minus LVAT from the "manual" measurements. As shown, the SDAT difference and LVAT difference over the 138 files indicates that the differences between the exemplary systems and methods and the "manual" calculations are small.

The exemplary method 200 may further include adjusting cardiac therapy 216 based on, or in response to, one or more metrics derived using the determined QRS onset and offset time values. Exemplary cardiac therapy may be further described herein with reference to FIGS. 19-21, which may be adjusted using the exemplary method 200. Additionally, the exemplary systems and methods described herein may further use or incorporated the systems and methods described in U.S. Pat. App. Pub. No. 2016/0045737 to Ghosh et al. published on Feb. 18, 2016, U.S. Pat. App. Pub. No. 2016/0045738 to Ghosh et al. published on Feb. 18, 2016, U.S. Pat. App. Pub. No. 2016/0045744 to Gillberg et al. published on Feb. 18, 2016, all of which are incorporated herein by reference in their entireties.

Additionally, the exemplary method 200 may be used with systems that include graphical user interfaces for use by users to evaluate a patient's cardiac health and/or adjust cardiac therapy. As described herein with reference to FIG. 1, the exemplary systems and methods described herein may use display apparatus 130 including a graphical user interface 132. The graphical user interface 132 may be configured to, among other things, present information for use in assisting a user in evaluating a cardiac pacing, or therapy, location, in assisting a user in assessing a patient's cardiac health, in assisting a user in navigating at least one implantable electrode to a region of the patient's heart, etc. For example, the graphical user interface 132 may be configured to display activation time information and heterogeneity metrics determined by method 200. Further, for example, the graphical user interface 132 may be configured to display a spatial map of electrical activation times based on geometric location of the electrodes relative to each other.

Further, the graphical user interface 132 may be configured to depict, or display, a graphical representation of cardiac electrical activation times from the monitored electrical activity about a portion of human anatomy monitored during intrinsic rhythm and/or during the delivery of cardiac therapy. In at least one embodiment, the cardiac electrical activation times may be represented about a portion of human anatomy by color scaling a portion of human anatomy on the graphical user interface 132 according to the surrogate cardiac electrical activation times. Additional exemplary graphical representations of surrogate electrical activation times that may utilize or be utilized by the exemplary systems and methods described herein may be described in U.S. Pat. App. Pub. No. 2015/0157231 to Gillberg et al. published on Jun. 11, 2015, U.S. Pat. App. Pub. No. 2015/0157232 to Gillberg et al. published on Jun. 11, 2015, U.S. Pat. App. Pub. No. 2015/0157865 to Gillberg et al. published on Jun. 11, 2015, and U.S. Pat. App. Pub. No. 2016/0030751 to Ghosh et al. published on Feb. 4, 2016, U.S. Patent Application Publication No. 2012/0284003 A1 published on Nov. 8, 2012 and entitled "Assessing Intra-Cardiac Activation Patterns" and U.S. Patent Application Publication No. 2012/0283587 A1 published on Nov. 8, 2012 and entitled "Assessing Intra-Cardiac Activation Patterns and Electrical Dyssynchrony," each of which is hereby incorporated by reference in its entirety.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 9-11.

Figure 19:
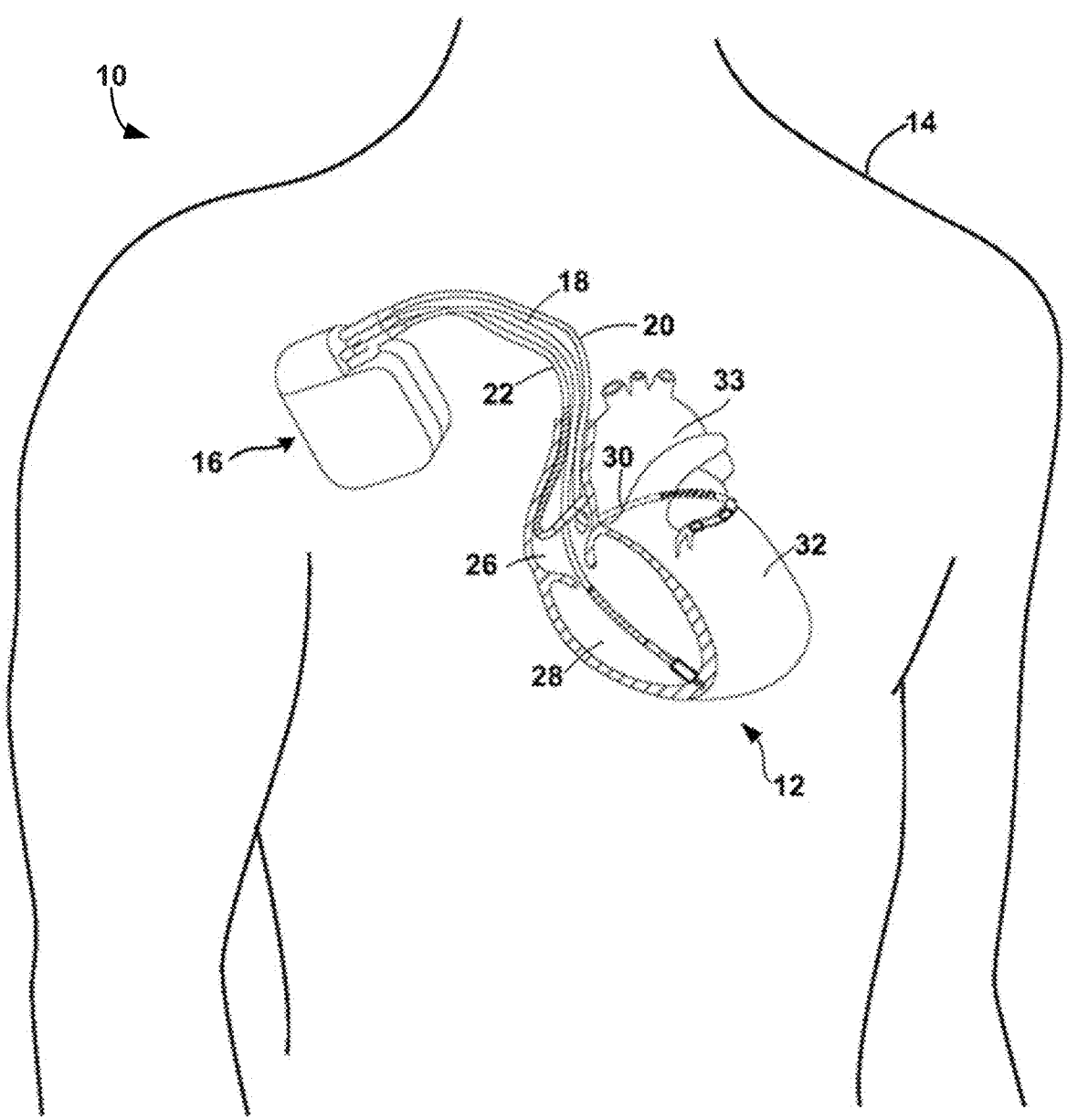
FIG. 19 is a diagram of an exemplary system including an exemplary implantable medical device (IMD).

FIG. 19 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 19, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 20A:
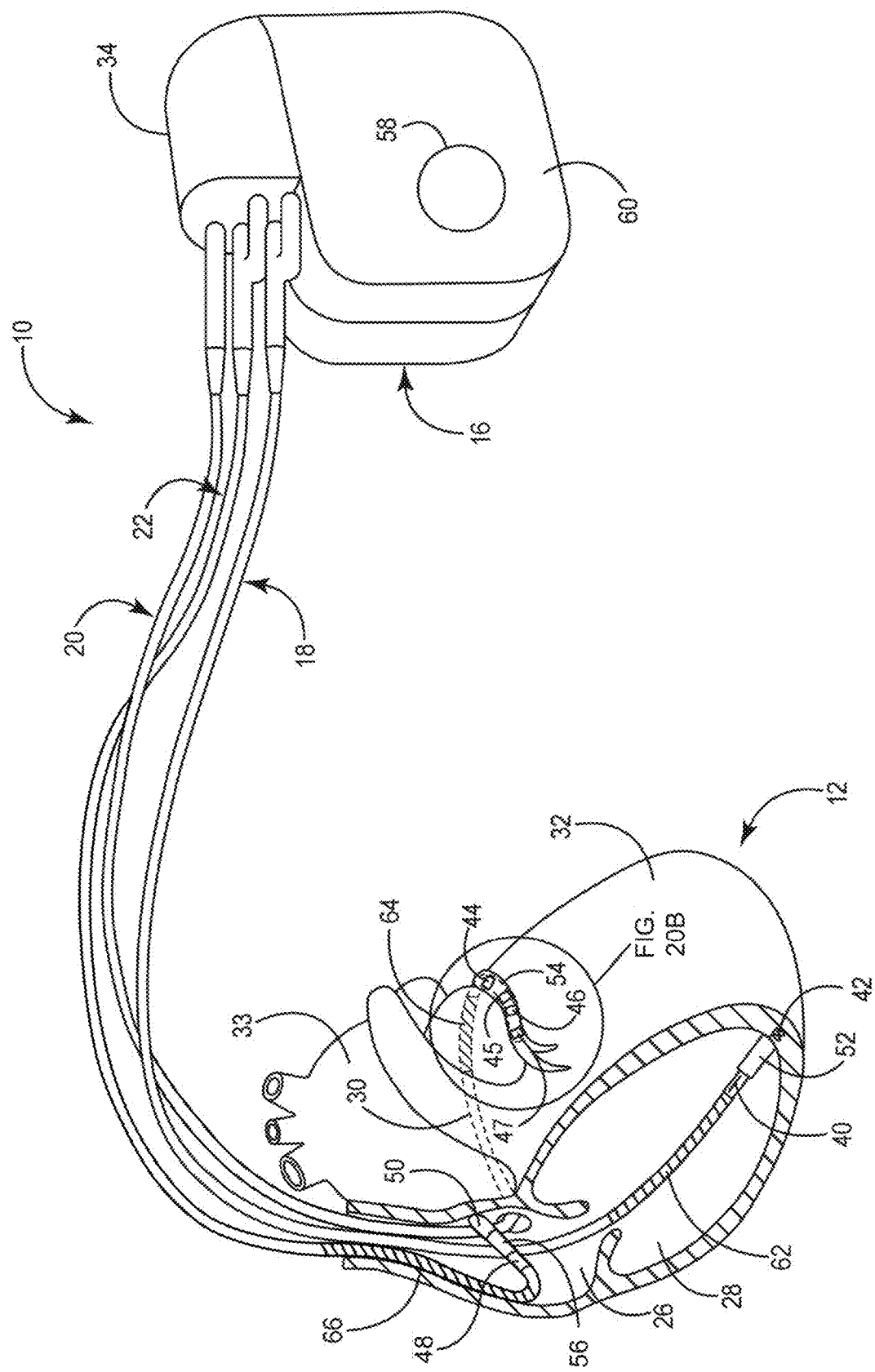
FIG. 20A is a diagram of the exemplary IMD of FIG. 20.
Figure 20B:
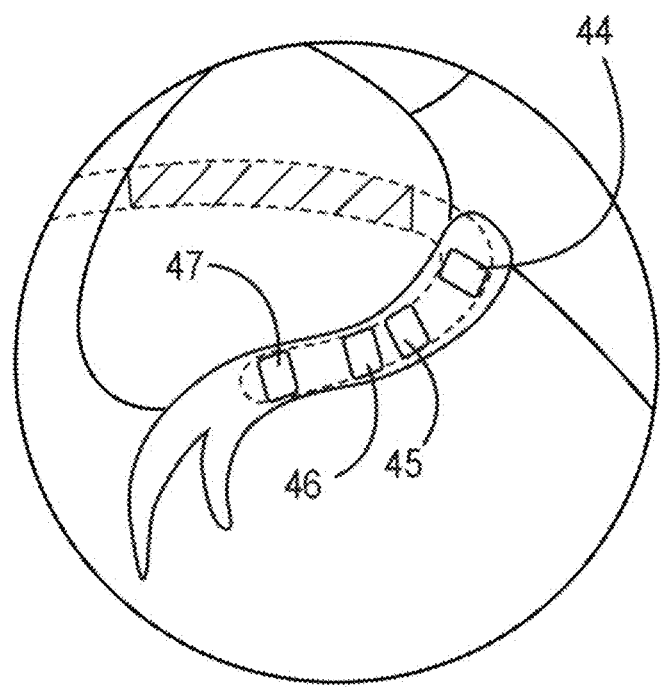
FIG. 20B is a diagram of an enlarged view of a distal end of the electrical lead disposed in the left ventricle of FIG. 20A.

FIGS. 20A-20B are conceptual diagrams illustrating the IMD 16 and the leads 18, 20, 22 of therapy system 10 of FIG. 19 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 20A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 20A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 19-21 is merely one example. In other examples, the therapy system may include epicardial leads and/or patch electrodes instead of or in addition to the transvenous leads 18, 20, 22 illustrated in FIG. 19. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 19). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 21A:
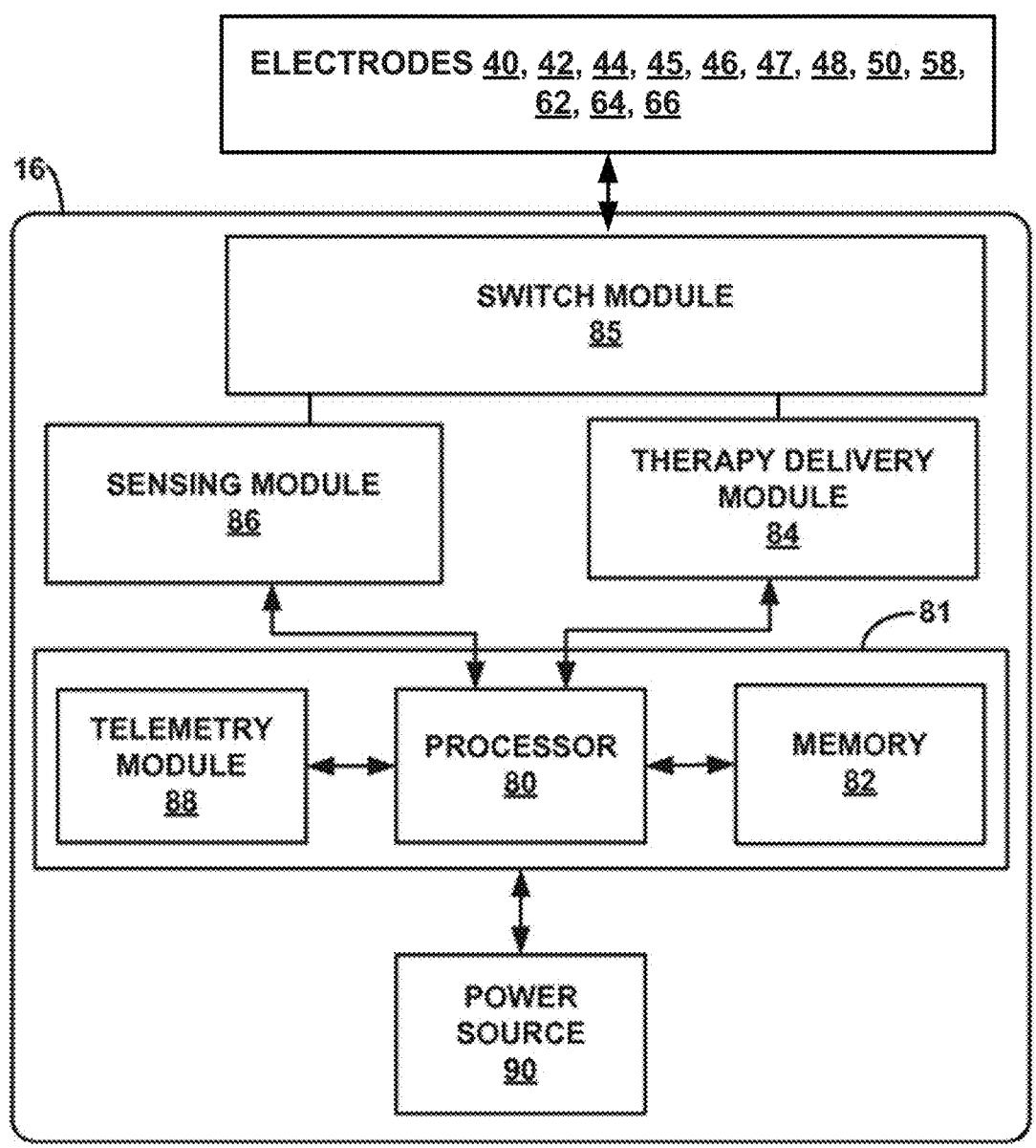
FIG. 21A is a block diagram of an exemplary IMD, e.g., of the systems of FIGS. 19-20.

FIG. 21A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 21B:
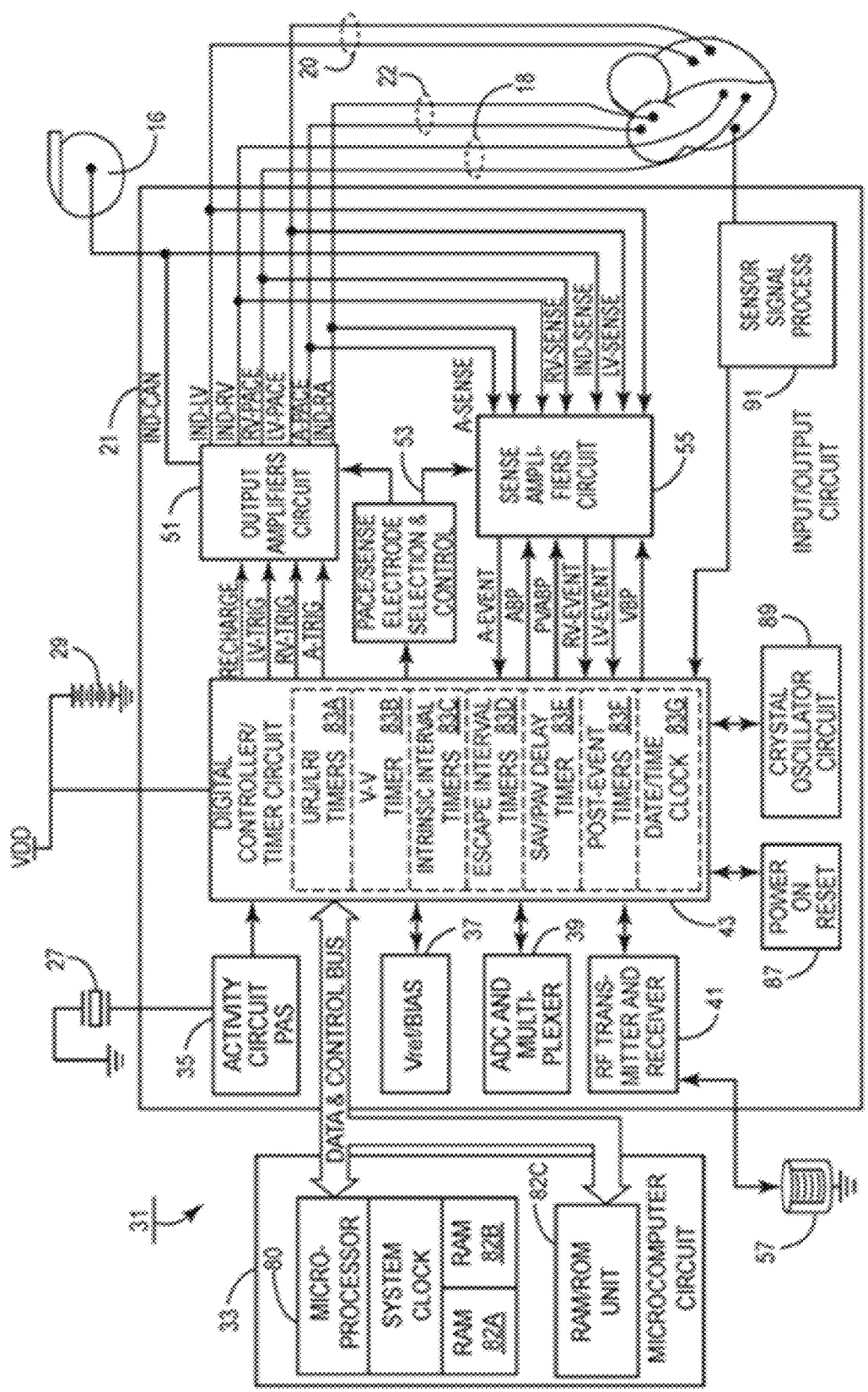
FIG. 21B is another block diagram of an exemplary IMD (e.g., an implantable pulse generator) circuitry and associated leads employed in the systems of FIGS. 19-20.

FIG. 21B is another embodiment of a functional block diagram for IMD 16. FIG. 21B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure Embodiment 1

A system comprising:
electrode apparatus comprising a plurality of electrodes to monitor electrical activity from tissue of a patient; and
computing apparatus comprising processing circuitry and coupled to the electrode apparatus, the computing apparatus configured to:
monitor electrical activity using the plurality of electrodes to generate a plurality of cardiac signals over time,
generate a dispersion signal from the plurality of cardiac signals, wherein the dispersion signal is representative of the dispersion of the plurality of cardiac signals over time, and
determine a QRS onset time value and a QRS offset time value for each of at least one QRS complex within the monitored electrical activity based on the dispersion signal.

Embodiment 2

A method comprising:
monitoring electrical activity from tissue of a patient using a plurality of electrodes to generate a plurality of cardiac signals over time;
generating a dispersion signal from the plurality of cardiac signals, wherein the dispersion signal is representative of the dispersion of the plurality of cardiac signals over time; and
determining a QRS onset time value and a QRS offset time value for each of at least one QRS complex within the monitored electrical activity based on the dispersion signal.

Embodiment 3

The system of embodiment 1 or the method of embodiment 2, wherein the computing apparatus is further configured to execute or the method further comprises determining an activation time for each of the at least one QRS complex within each of the plurality of cardiac signals within the QRS duration between the QRS onset and offset time values corresponding to the at least one QRS complex.

Embodiment 4

The system or method of embodiment 3, wherein the computing apparatus is further configured to execute or the method further comprises determining at least one metric of electrical heterogeneity based on the activation time for each of the at least one QRS complex within each of the plurality of cardiac signals.

Embodiment 5

The systems or methods as set forth in any one of embodiments 1-4, wherein the plurality of electrodes comprises a plurality of external electrodes to be located proximate the patient's skin.

Embodiment 6

The systems or methods as set forth in embodiments 1-5, wherein the plurality of electrodes comprises a plurality of internal electrodes to be located within the patient.

Embodiment 7

The systems or methods as set forth in any one of embodiments 1-6, wherein generating a dispersion signal from the plurality of cardiac signals comprises determining a standard deviation of the plurality of cardiac signals over time.

Embodiment 8

The systems or methods as set forth in any one of embodiments 1-7, wherein the computing apparatus is further configured to execute or the method further comprises selecting a portion of the dispersion signal over a selected time period, and
wherein determining a QRS onset time value and a QRS offset time value for each of at least one QRS complex within the monitored electrical activity based on the dispersion signal comprises determining the QRS onset time value and the QRS offset time value for each of the at least one QRS complex within the monitored electrical activity of the selected time period based on the selected portion of the dispersion signal.

Embodiment 9

The systems or methods of embodiment 8, wherein the selected time period is less than or equal to 5 seconds.

Embodiment 10

The systems or methods as set forth in any one of embodiments 1-9, wherein determining a QRS onset time value and a QRS offset time value for each of at least one QRS complex within the monitored electrical activity based on the dispersion signal further comprises:
determining a maximum dispersion value of the dispersion signal; and
determining the QRS onset time value and the QRS offset time value using the maximum dispersion value.

Embodiment 11

The systems or methods of embodiment 10, wherein determining a QRS onset time value and a QRS offset time value for each of at least one QRS complex within the monitored electrical activity based on the dispersion signal further comprises:
filtering the dispersion signal to remove one or more values of the dispersion signal that are less than or equal to a selected percentage of the maximum dispersion value of the dispersion signal.

Embodiment 12

The systems or methods of embodiment 10, wherein determining a QRS onset time value and a QRS offset time value for each of at least one QRS complex within the monitored electrical activity based on the dispersion signal further comprises:
filtering the dispersion signal to remove one or more dispersion values of the dispersion signal corresponding to at least one of a T-wave and a P-wave in the plurality of cardiac signals.

Embodiment 13

The systems or methods as set forth in any one of embodiments 1-12, wherein determining a QRS onset time value and a QRS offset time value for each of at least one QRS complex within the monitored electrical activity based on the dispersion signal further comprises:
determining a minimum dispersion value of the dispersion signal within a first time period before a maximum dispersion value of the dispersion signal to determine the QRS onset time value, and
determining a minimum dispersion value of the dispersion signal within a second time period after the maximum dispersion value of the dispersion signal to determine the QRS offset time value.

Embodiment 14

The systems or methods of embodiment 13, wherein each of the first and second time periods are less than or equal to 200 milliseconds.

Embodiment 15

The systems or methods as set forth in any one of embodiments 1-14, wherein determining a QRS onset time value and a QRS offset time value for each of at least one QRS complex within the monitored electrical activity based on the dispersion signal further comprises:
determining a latest dispersion value of the dispersion signal within a first time period before a maximum dispersion value of the dispersion signal that is less than or equal to a selected percentage of a minimum dispersion value of the dispersion signal within the first time period to determine the QRS onset time value, and
determining an earliest dispersion value of the dispersion signal within a second time period after the maximum dispersion value of the dispersion signal that is less than or equal to a selected percentage of a minimum dispersion value of the dispersion signal within the second time period to determine the QRS onset time value

Embodiment 16

The systems or methods as set forth in any one of embodiments 1-15, wherein the computing apparatus is further configured to execute or the method further comprises:

determining an absolute amplitude between the QRS onset time value and the QRS offset time value for each of the at least QRS complex for each of the plurality of cardiac signals;

selecting one or more cardiac signals of the plurality of cardiac signals based on the absolute amplitude; and determining an activation time for each of the at least one QRS complex within each of the selected one or more cardiac signals within the QRS duration between the QRS onset and offset time values corresponding to the at least one QRS complex.

Embodiment 17

The systems or methods of embodiment 16, wherein selecting one or more cardiac signals of the plurality of cardiac signals based on the absolute amplitude comprises selecting one or more cardiac signals of the plurality of cardiac signals defining an absolute amplitude greater than or equal to a threshold value, wherein the threshold value is less than the median absolute amplitude of the plurality of cardiac signals.

Embodiment 18

The systems or methods as set forth in any one of embodiments 1-17, wherein the computing apparatus is further configured to execute or the method further comprises removing one or more noisy cardiac signals from the plurality of cardiac signals prior to determining the dispersion signal.

Embodiment 19

The systems or methods of embodiment 18, wherein the one or more noisy cardiac signals are identified by identifying cardiac signals comprising absolute areas-under-the-curve greater than or equal to a threshold value.

Embodiment 20

The systems or methods as set forth in any one of embodiments 1-19, wherein the at least one QRS complex comprises a plurality of QRS complexes.

Embodiment 21

The systems or methods as set forth in any one of embodiments 1-20, wherein the computing apparatus is further configured to execute or the method further comprises adjusting cardiac therapy in response to one or more metrics derived using the determined QRS onset and offset time values, wherein the one or more metrics comprise activation time of each of the plurality of cardiac signals.

Embodiment 22

The systems or methods as set forth in any one of embodiments 1-21, wherein the computing apparatus is further configured to execute or the method further comprises displaying on a graphical user interface one or more metrics derived using the determined QRS onset and offset time values, wherein the one or more metrics comprise activation time of each of the plurality of cardiac signals.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system comprising:
   electrode apparatus comprising a plurality of electrodes to monitor electrical activity from tissue of a patient; and
   computing apparatus comprising processing circuitry and coupled to the electrode apparatus, the computing apparatus configured to:
   monitor electrical activity using the plurality of electrodes to generate a plurality of cardiac signals over time,
   generate a dispersion signal from the plurality of cardiac signals, wherein the dispersion signal is representative of the dispersion of the plurality of cardiac signals over time, and
   determine a QRS onset time value and a QRS offset time value for each of at least one QRS complex within the monitored electrical activity based on the dispersion signal.

2. The system of claim 1, wherein the computing apparatus is further configured to determine an activation time for each of the at least one QRS complex within each of the plurality of cardiac signals within the QRS duration between the QRS onset and offset time values corresponding to the at least one QRS complex.

3. The system of claim 2, wherein the computing apparatus is further configured to determine at least one metric of electrical heterogeneity based on the activation time for each of the at least one QRS complex within each of the plurality of cardiac signals.

4. The system of claim 1, wherein the plurality of electrodes comprises a plurality of external electrodes to be located proximate the patient's skin.

5. The system of claim 1, wherein the plurality of electrodes comprises a plurality of internal electrodes to be located within the patient.

6. The system of claim 1, wherein generating a dispersion signal from the plurality of cardiac signals comprises determining a standard deviation of the plurality of cardiac signals over time.

7. The system of claim 1, wherein the computing apparatus is further configured to select a portion of the dispersion signal over a selected time period, and
   wherein determining a QRS onset time value and a QRS offset time value for each of at least one QRS complex within the monitored electrical activity based on the dispersion signal comprises determining the QRS onset time value and the QRS offset time value for each of the at least one QRS complex within the monitored electrical activity of the selected time period based on the selected portion of the dispersion signal.

8. The system of claim 1, wherein determining a QRS onset time value and a QRS offset time value for each of at least one QRS complex within the monitored electrical activity based on the dispersion signal further comprises:
   determining a maximum dispersion value of the dispersion signal; and
   determining the QRS onset time value and the QRS offset time value using the maximum dispersion value.

9. The system of claim 1, wherein determining a QRS onset time value and a QRS offset time value for each of at least one QRS complex within the monitored electrical activity based on the dispersion signal further comprises:
determining a minimum dispersion value of the dispersion signal within a first time period before a maximum dispersion value of the dispersion signal to determine the QRS onset time value, and
determining a minimum dispersion value of the dispersion signal within a second time period after the maximum dispersion value of the dispersion signal to determine the QRS offset time value.

10. The system of claim 1, wherein determining a QRS onset time value and a QRS offset time value for each of at least one QRS complex within the monitored electrical activity based on the dispersion signal further comprises:
determining a latest dispersion value of the dispersion signal within a first time period before a maximum dispersion value of the dispersion signal that is less than or equal to a selected percentage of a minimum dispersion value of the dispersion signal within the first time period to determine the QRS onset time value, and
determining an earliest dispersion value of the dispersion signal within a second time period after the maximum dispersion value of the dispersion signal that is less than or equal to a selected percentage of a minimum dispersion value of the dispersion signal within the second time period to determine the QRS onset time value.

11. The system of claim 1, wherein the computing apparatus is further configured to:
determine an absolute amplitude between the QRS onset time value and the QRS offset time value for each of the at least QRS complex for each of the plurality of cardiac signals;
select one or more cardiac signals of the plurality of cardiac signals based on the absolute amplitude; and
determine an activation time for each of the at least one QRS complex within each of the selected one or more cardiac signals within the QRS duration between the QRS onset and offset time values corresponding to the at least one QRS complex.

12. The system of claim 1, wherein the computing apparatus is further configured to remove one or more noisy cardiac signals from the plurality of cardiac signals prior to determining the dispersion signal, wherein the one or more noisy cardiac signals are identified by identifying cardiac signals comprising absolute areas-under-the-curve greater than or equal to a threshold value.

13. The system of claim 1, wherein the computing apparatus is further configured to display on a graphical user interface one or more metrics derived using the determined QRS onset and offset time values, wherein the one or more metrics comprise activation time of each of the plurality of cardiac signals.

14. A method comprising:
monitoring electrical activity from tissue of a patient using a plurality of electrodes to generate a plurality of cardiac signals over time;
generating a dispersion signal from the plurality of cardiac signals, wherein the dispersion signal is representative of the dispersion of the plurality of cardiac signals over time; and
determining a QRS onset time value and a QRS offset time value for each of at least one QRS complex within the monitored electrical activity based on the dispersion signal.

15. The method of claim 14 further comprising determining an activation time for each of the at least one QRS complex within each of the plurality of cardiac signals within the QRS duration between the QRS onset and offset time values corresponding to the at least one QRS complex.

16. The method of claim 15 further comprising determining at least one metric of electrical heterogeneity based on the activation time for each of the at least one QRS complex within each of the plurality of cardiac signals.

17. The method of claim 14, wherein generating a dispersion signal from the plurality of cardiac signals comprises determining a standard deviation of the plurality of cardiac signals over time.

18. The method of claim 14 further comprising selecting a portion of the dispersion signal over a selected time period, and
wherein determining a QRS onset time value and a QRS offset time value for each of at least one QRS complex within the monitored electrical activity based on the dispersion signal comprises determining the QRS onset time value and the QRS offset time value for each of the at least one QRS complex within the monitored electrical activity of the selected time period based on the selected portion of the dispersion signal.

19. The method of claim 14, wherein determining a QRS onset time value and a QRS offset time value for each of at least one QRS complex within the monitored electrical activity based on the dispersion signal further comprises:
determining a maximum dispersion value of the dispersion signal; and
determining the QRS onset time value and the QRS offset time value using the maximum dispersion value.

20. The method of claim 19, wherein determining a QRS onset time value and a QRS offset time value for each of at least one QRS complex within the monitored electrical activity based on the dispersion signal further comprises:
filtering the dispersion signal to remove one or more values of the dispersion signal that are less than or equal to a selected percentage of the maximum dispersion value of the dispersion signal.

21. The method of claim 19, wherein determining a QRS onset time value and a QRS offset time value for each of at least one QRS complex within the monitored electrical activity based on the dispersion signal further comprises:
filtering the dispersion signal to remove one or more dispersion values of the dispersion signal corresponding to at least one of a T-wave and a P-wave in the plurality of cardiac signals.

22. The method of claim 14, wherein determining a QRS onset time value and a QRS offset time value for each of at least one QRS complex within the monitored electrical activity based on the dispersion signal further comprises:
determining a latest dispersion value of the dispersion signal within a first time period before a maximum dispersion value of the dispersion signal that is less than or equal to a selected percentage of a minimum dispersion value of the dispersion signal within the first time period to determine the QRS onset time value, and
determining an earliest dispersion value of the dispersion signal within a second time period after the maximum dispersion value of the dispersion signal that is less than or equal to a selected percentage of a minimum dispersion value of the dispersion signal within the second time period to determine the QRS onset time value.

23. The method of claim 22, wherein each of the first and second time periods are less than or equal to 200 milliseconds.

24. The method of claim 14 further comprising:
- determining an absolute amplitude between the QRS onset time value and the QRS offset time value for each of the at least QRS complex for each of the plurality of cardiac signals;
- selecting one or more cardiac signals of the plurality of cardiac signals based on the absolute amplitude; and
- determining an activation time for each of the at least one QRS complex within each of the selected one or more cardiac signals within the QRS duration between the QRS onset and offset time values corresponding to the at least one QRS complex.

25. The method of claim 14 further comprising adjusting cardiac therapy in response to one or more metrics derived using the determined QRS onset and offset time values, wherein the one or more metrics comprise activation time of each of the plurality of cardiac signals.

26. A system comprising:
- electrode apparatus comprising a plurality of electrodes to monitor electrical activity from tissue of a patient; and
- computing apparatus comprising processing circuitry and coupled to the electrode apparatus, the computing apparatus configured to:
    - monitor electrical activity using the plurality of electrodes to generate a plurality of cardiac signals over time,
    - determine a standard deviation of the plurality of cardiac signals over time, and
    - determine a QRS onset time value and a QRS offset time value for each of at least one QRS complex within the monitored electrical activity based on the determined standard deviation.

* * * * *